United States Patent
Lin et al.

(10) Patent No.: US 11,597,773 B2
(45) Date of Patent: Mar. 7, 2023

(54) CD6 ANTIBODY FOR TREATMENT OF T-CELL MEDIATED DISEASES OR DISORDERS

(71) Applicants: THE CLEVELAND CLINIC FOUNDATION, Cleveland, OH (US); The Regents of the University of Michigan, Ann Arbor, MI (US)

(72) Inventors: Feng Lin, Willoughby, OH (US); David A. Fox, Ann Arbor, MI (US)

(73) Assignees: THE CLEVELAND CLINIC FOUNDATION, Cleveland, OH (US); THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 586 days.

(21) Appl. No.: 16/743,278

(22) Filed: Jan. 15, 2020

(65) Prior Publication Data
US 2020/0140566 A1  May 7, 2020

Related U.S. Application Data

(63) Continuation of application No. 15/623,729, filed on Jun. 15, 2017, now Pat. No. 10,562,975.

(60) Provisional application No. 62/350,218, filed on Jun. 15, 2016.

(51) Int. Cl.
*C07K 16/28* (2006.01)
*A61K 39/00* (2006.01)

(52) U.S. Cl.
CPC .... *C07K 16/2896* (2013.01); *A61K 2039/505* (2013.01); *C07K 2317/21* (2013.01); *C07K 2317/24* (2013.01); *C07K 2317/51* (2013.01); *C07K 2317/515* (2013.01); *C07K 2317/54* (2013.01); *C07K 2317/55* (2013.01); *C07K 2317/76* (2013.01); *C07K 2317/92* (2013.01); *C07K 2319/30* (2013.01)

(58) Field of Classification Search
None
See application file for complete search history.

(56) References Cited

U.S. PATENT DOCUMENTS 5,859,205 A    1/1999  Adair et al.
10,562,975 B2 *  2/2020  Lin ................... C07K 16/2896

FOREIGN PATENT DOCUMENTS

| CN | 104497141 A | 4/2015 |
| WO | 98/03551 | 1/1998 |
| WO | 2009/113083 | 9/2009 |

OTHER PUBLICATIONS

Chinese Office Action for corresponding Chinese Application Serial No. 201780037525.4 dated Sep. 16, 2021, pp. 1-15.
Brown et al. (J Immunol. May 1, 1996; 156(9):3285-91). (Year 1996).
Eduardo Padian, Mol Immunol. Feb. 1994; 31(3): 169-217. (Year: 1994).
Vajdos et al. (J Mol Biol. 20025 Jul 5; 320(2): 415-28) (Year: 2002).
Bedouelle et al. (FEBS J. Jan. 2006; 273(1):34-46). (Year: 2006).
Itolizumab Injection pamphlet, Biocon, 2013, pp. 1-2. (Year: 2013).
Colman (Research in Immunology, 145:33-36, 1994) (Year: 1994).
Rudikoff et al. (Proc. Natl. Acad. Sci. USA, 79: 1979-1983, Mar. 1982) (Year: 1982).
Li, Yan, et al. "CD6 as a potential target for treating multiple sclerosis." Proceedings of the National Academy of Sciences 114.10 (2017): 2687-2692.
Lin, F., "Humanized Anti-CD6 mAb for Treating of Autoimmune Diseases," Cleveland Clinic Innovations, Jun. 2, 2016 (Jan. 2, 2016). Retrieved from http://innovations.clevelandclinic.org/Technology/Innovation-Catalog/PDFs/Humanized-Anti-CD6.aspx. Retrieved on Sep. 4, 2017.
Alonso, R. et al., "Towards the Definition of a Chimpanzee and Human Conserved CD6 Domain 1 Epitope Recognized by T1 Monoclonal Antibody," HYBRIDOMA, vol. 27, No. 4, Aug. 1, 2008, pp. 291-301.
Roshni, M. et al., "Itolizumab—a humanized anit-CD6 monoclonal antibody with a better side effects profile for the treatment of psoriasis," Clinical, Cosmetic and Investigational Dermatology, Apr. 1, 2015, p. 215.
International Search Report corresponding to International Application No. PCT/US2017/037639 dated Sep. 2, 2017, pp. 1-13.

\* cited by examiner

*Primary Examiner* — Zachary S Skelding
(74) *Attorney, Agent, or Firm* — Tarolli, Sundheim, Covell & Tummino LLP

(57) ABSTRACT

A method of treating a T-cell mediated disease in a subject by administering to the subject a therapeutically effective amount of an antibody or fragment thereof that specifically binds to CD6 is described. Humanized antibodies useful for the method are also described.

18 Claims, 15 Drawing Sheets

Specification includes a Sequence Listing.

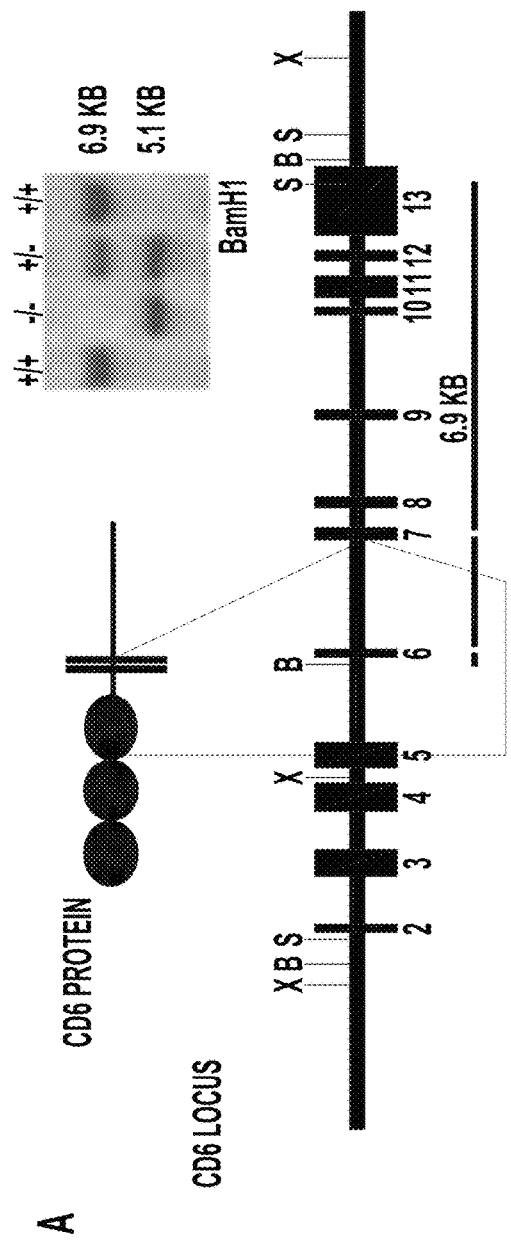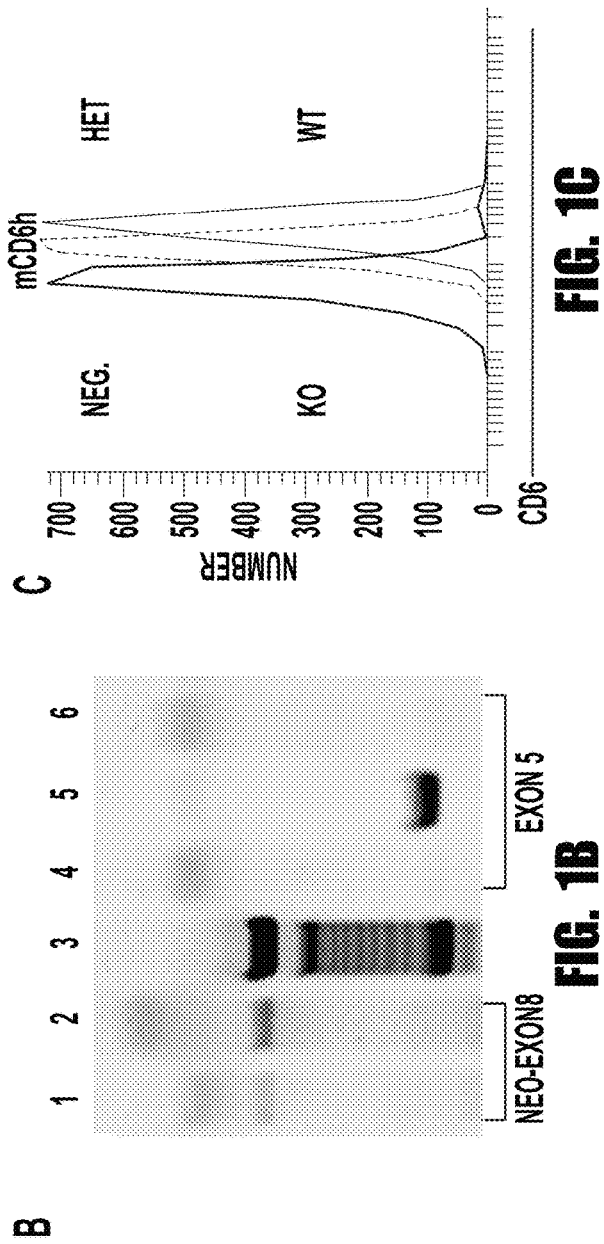
FIG. 1A
FIG. 1B
FIG. 1C

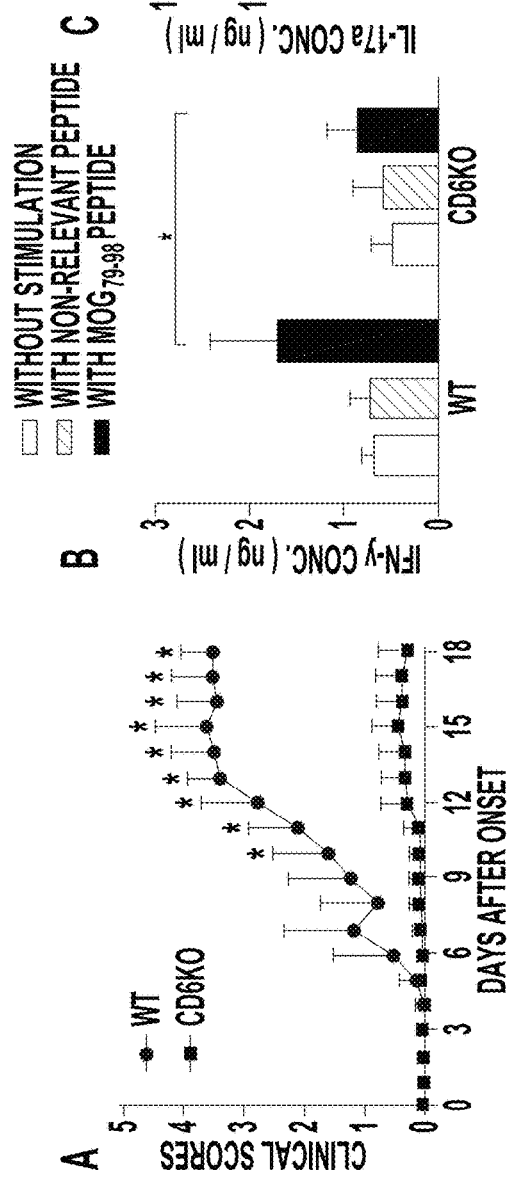

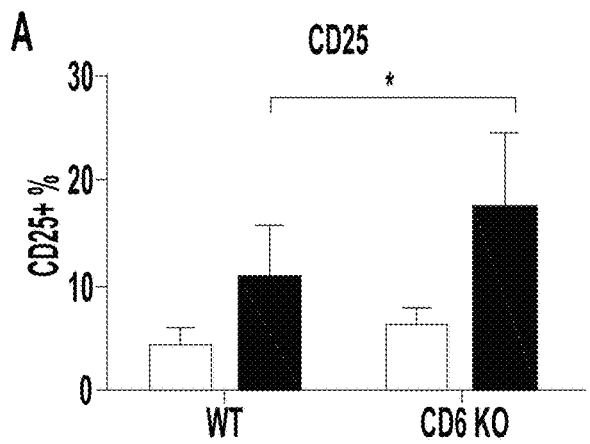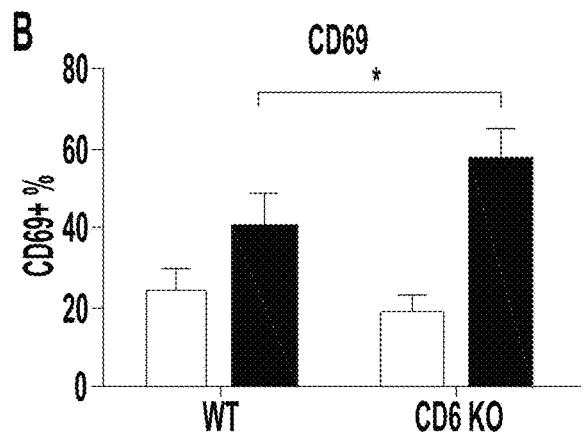
FIG. 4A  FIG. 4B
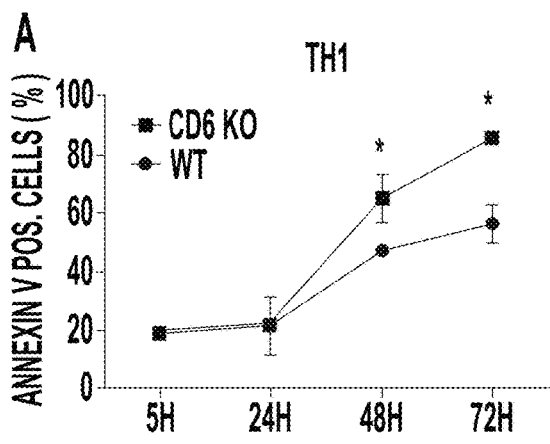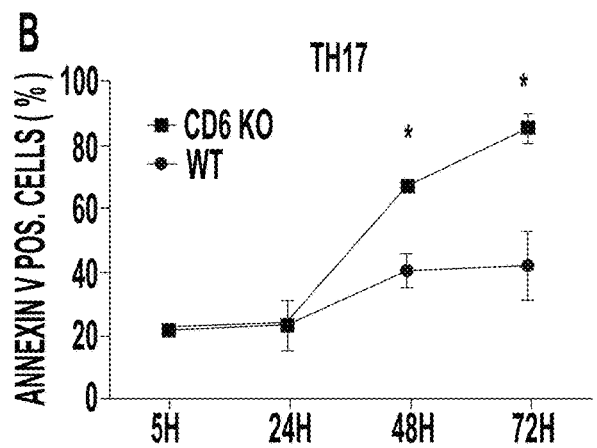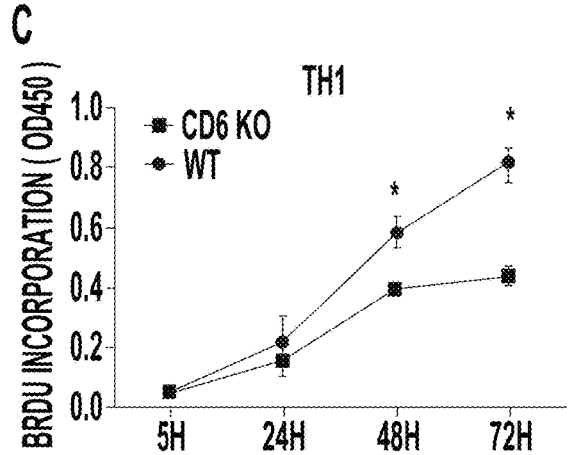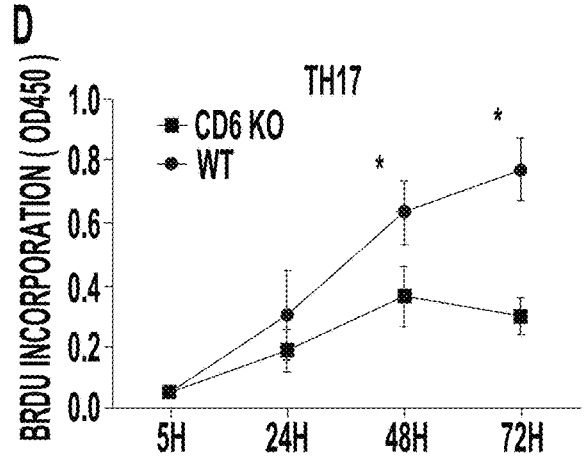
FIG. 5A  FIG. 5B  FIG. 5C  FIG. 5D

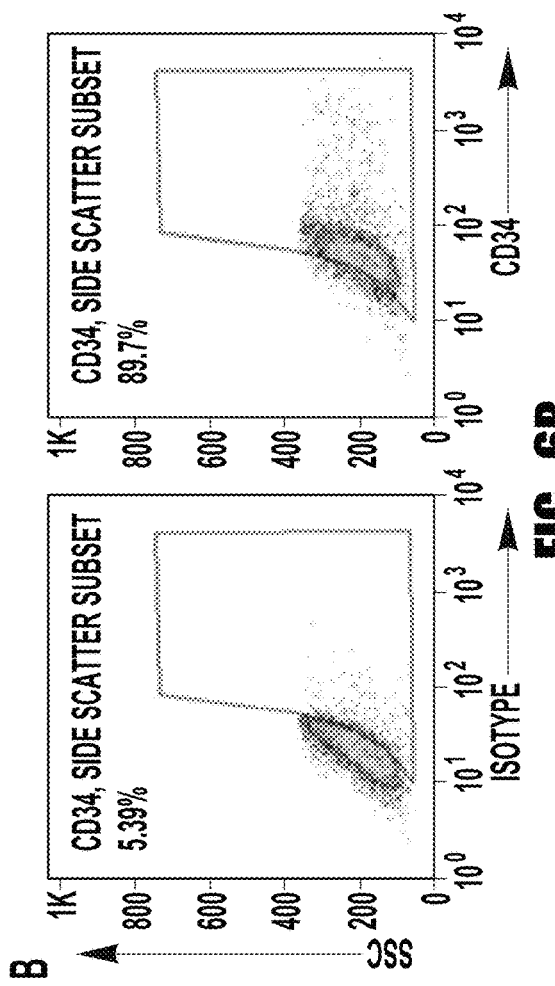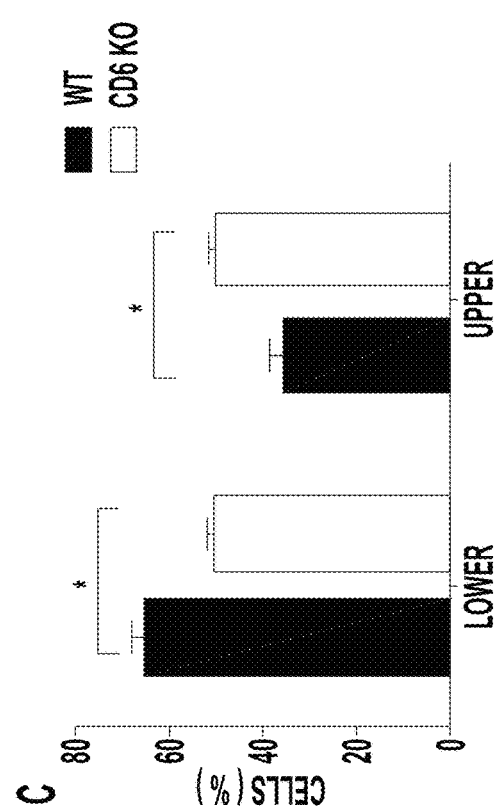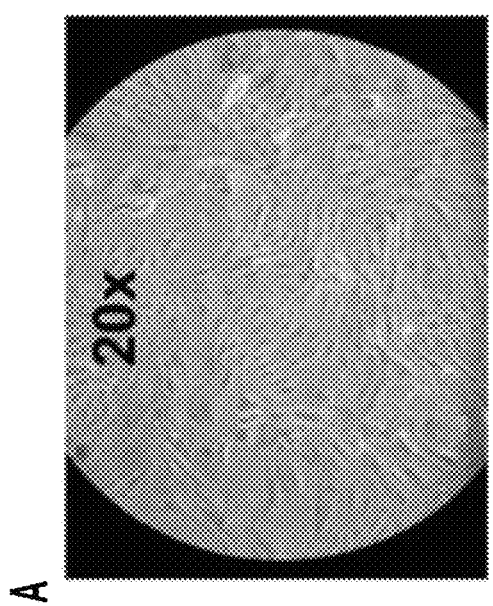
FIG. 6A
FIG. 6B
FIG. 6C

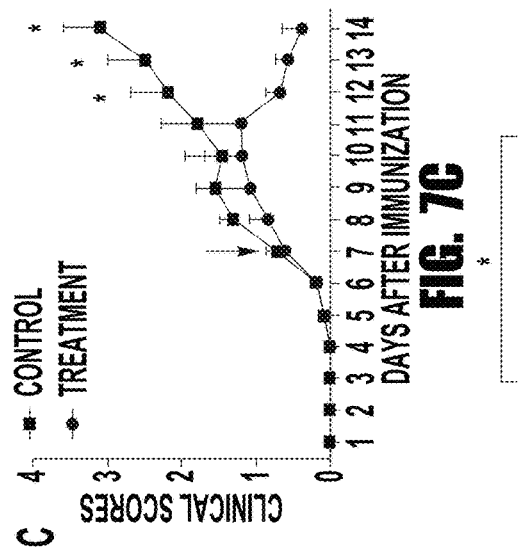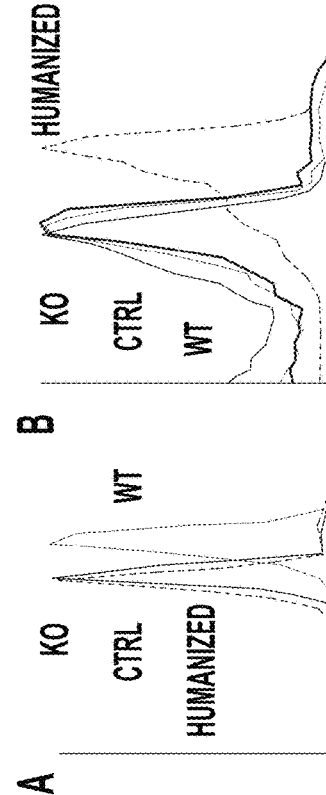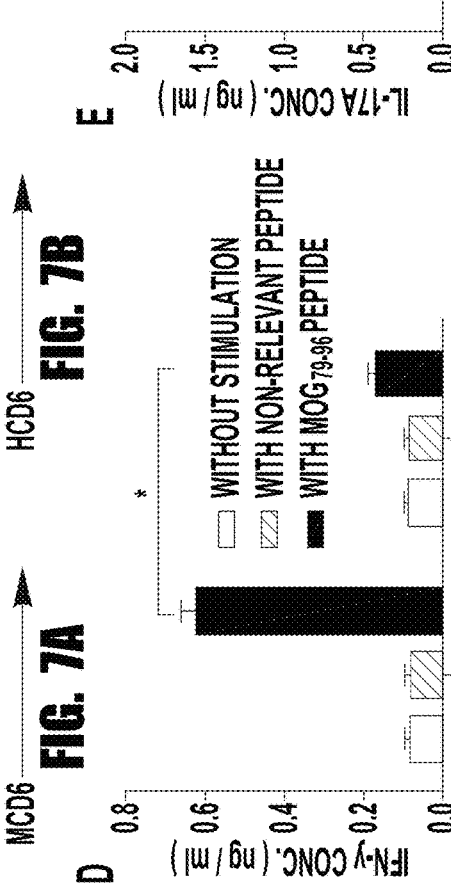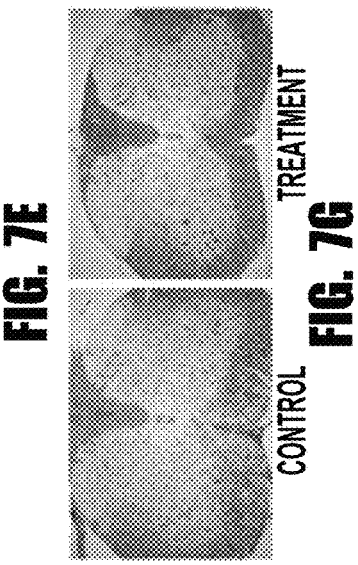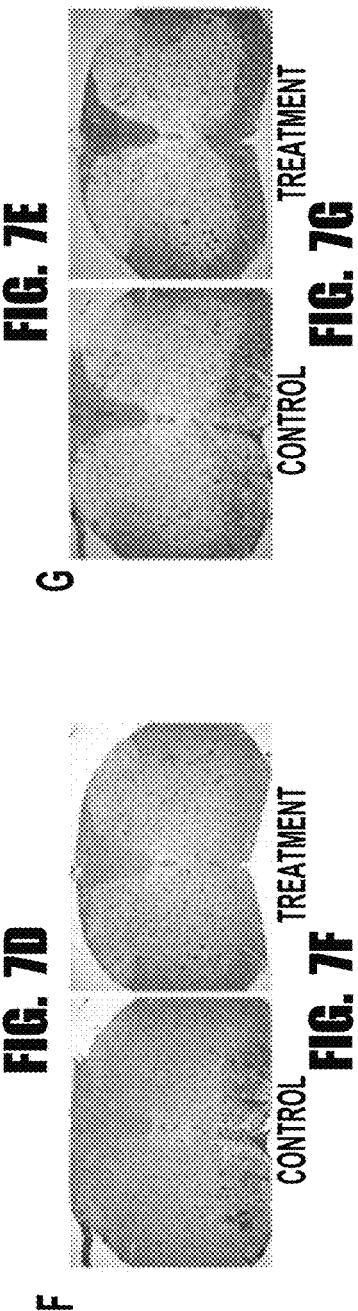

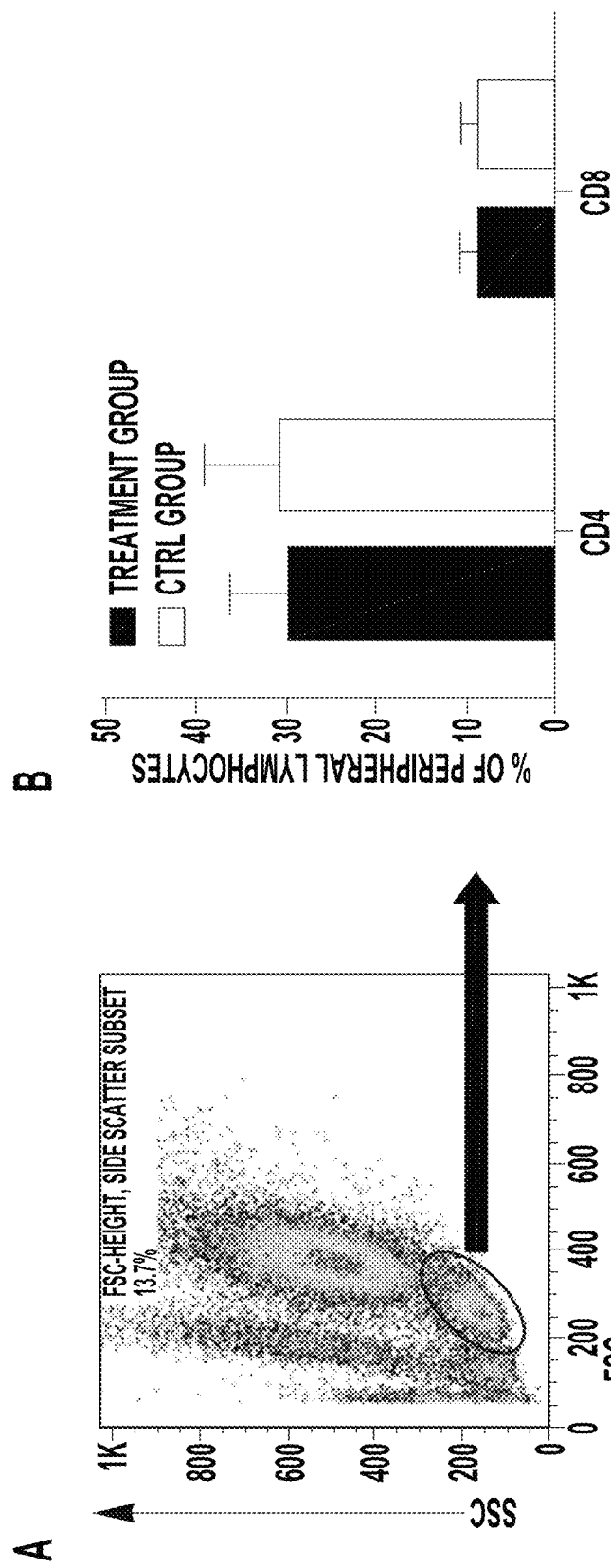

A  V$_H$2-hIgG1C$_H$ DNA sequence
GCCGCCACCATGGGCTGGAGCTGGATCCTGCTGTTCCTCCTGAGCGTGACAGCAGGA
GTGCACAGCCAAGTCCAACTGCAAGAATCGGGTCCGGGCCTGGTGAAACCGTCGGA
AACGCTGTCGCTGACCTGTACCGTGTCGGGCTTTAGCCTGAGCCGTTATAGCGTGCA
TTGGGTTCGCCAGCCGCCGGGTAAAGGCCTGGAATGGCTGGGTCTGATTTGGGGCG
GTGGCTTTACCGATTATAACAGCGCGCTGAAAAGCCGTCTGACCATCAGCAAAGAT
AACAGCAAAAATCAGGTGAGCCTGAAACTGAGCAGCGTTACCGCGGCCGATACCGC
CGTGTATTATTGTGCTCGTGAAGGTGTCGCATACTGGGGTCAAGGCACGCTGGTTAC
CGTTAGTTCCGCTAGCACCAAGGGCCCATCGGTCTTCCCCCTGGCACCCTCCTCCAA
GAGCACCTCTGGGGGCACAGCGGCCCTGGGCTGCCTGGTCAAGGACTACTTCCCCG
AACCGGTGACGGTGTCGTGGAACTCAGGCGCCCTGACCAGCGGCGTGCACACCTTC
CCGGCTGTCCTACAGTCCTCAGGACTCTACTCCCTCAGCAGCGTGGTGACCGTGCCC
TCCAGCAGCTTGGGCACCCAGACCTACATCTGCAACGTGAATCACAAGCCCAGCAA
CACCAAGGTGGACAAGAAAGTTGAGCCCAAATCTTGTGACAAAACTCACACATGCC
CACCGTGCCCAGCACCTGAACTCCTGGGGGGACCGTCAGTCTTCCTCTTCCCCCCAA
AACCCAAGGACACCCTCATGATCTCCCGGACCCCTGAGGTCACATGCGTGGTGGTG
GACGTGAGCCACGAAGACCCTGAGGTCAAGTTCAACTGGTACGTGGACGGCGTGGA
GGTGCATAATGCCAAGACAAAGCCGCGGGAGGAGCAGTACAACAGCACGTACCGT
GTGGTCAGCGTCCTCACCGTCCTGCACCAGGACTGGCTGAATGGCAAGGAGTACAA
GTGCAAGGTCTCCAACAAAGCCCTCCCAGCCCCCATCGAGAAAACCATCTCCAAAG
CCAAAGGGCAGCCCCGAGAACCACAGGTGTACACCCTGCCCCCATCCCGGGATGAG
CTGACCAAGAACCAGGTCAGCCTGACCTGCCTGGTCAAAGGCTTCTATCCCAGCGAC
ATCGCCGTGGAGTGGGAGAGCAATGGGCAGCCGGAGAACAACTACAAGACCACGC
CTCCCGTGCTGGACTCCGACGGCTCCTTCTTCCTCTACAGCAAGCTCACCGTGGACA
AGAGCAGGTGGCAGCAGGGGAACGTCTTCTCATGCTCCGTGATGCATGAGGCTCTG
CACAACCACTACACGCAGAAGAGCCTCTCCCTGTCTCCGGGTAAATGA

FIG. 16A

B  V$_H$2-hIgG1C$_H$ Amino acid sequence
AATMGWSWILLFLLSVTAGVHSQVQLQESGPGLVKPSETLSLTCTVSGFSLSRYSVHWV
RQPPGKGLEWLGLIWGGGFTDYNSALKSRLTISKDNSKNQVSLKLSSVTAADTAVYYC
AREGVAYWGQGTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKVDKKVEPK
SCDKTHTCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTI
SKAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPGK*

FIG. 16B

A  V$_H$4-hIgG1C$_H$ DNA sequence
GCCGCCACCATGGGCTGGAGCTGGATCCTGCTGTTCCTCCTGAGCGTGACAGCAGGA
GTGCACAGCCAAGTCCAACTGCAAGAATCTGGTCCGGGTCTGGTGAAACCGTCGGA
AACGCTGTCGCTGACGTGTACCGTGTCGGGCTTTAGCATTAGCCGTTATAGCGTTCA
TTGGATTCGCCAGCCGCCGGGTAAAGGCCTGGAATGGATTGGTCTGATCTGGGGCG
GTGGCTTTACCGATTATAACAGCGCGCTGAAAAGCCGTGTGACCATCAGCAAAGAT
AACAGCAAAAATCAGGTGAGCCTGAAACTGAGCAGCGTTACCGCGGCCGATACCGC
CGTGTATTATTGCGCTCGTGAAGGCGTCGCTTACTGGGGCCAAGGCACCCTGGTTAC
GGTCTCGTCGGCTAGCACCAAGGGCCCATCGGTCTTCCCCCTGGCACCCTCCTCCAA
GAGCACCTCTGGGGGCACAGCGGCCCTGGGCTGCCTGGTCAAGGACTACTTCCCCG
AACCGGTGACGGTGTCGTGGAACTCAGGCGCCCTGACCAGCGGCGTGCACACCTTC
CCGGCTGTCCTACAGTCCTCAGGACTCTACTCCCTCAGCAGCGTGGTGACCGTGCCC
TCCAGCAGCTTGGGCACCCAGACCTACATCTGCAACGTGAATCACAAGCCCAGCAA
CACCAAGGTGGACAAGAAAGTTGAGCCCAAATCTTGTGACAAAACTCACACATGCC
CACCGTGCCCAGCACCTGAACTCCTGGGGGGACCGTCAGTCTTCCTCTTCCCCCCAA
AACCCAAGGACACCCTCATGATCTCCCGGACCCCTGAGGTCACATGCGTGGTGGTG
GACGTGAGCCACGAAGACCCTGAGGTCAAGTTCAACTGGTACGTGGACGGCGTGGA
GGTGCATAATGCCAAGACAAAGCCGCGGGAGGAGCAGTACAACAGCACGTACCGT
GTGGTCAGCGTCCTCACCGTCCTGCACCAGGACTGGCTGAATGGCAAGGAGTACAA
GTGCAAGGTCTCCAACAAAGCCCTCCCAGCCCCCATCGAGAAAACCATCTCCAAAG
CCAAAGGGCAGCCCCGAGAACCACAGGTGTACACCCTGCCCCCATCCCGGGATGAG
CTGACCAAGAACCAGGTCAGCCTGACCTGCCTGGTCAAAGGCTTCTATCCCAGCGAC
ATCGCCGTGGAGTGGGAGAGCAATGGGCAGCCGGAGAACAACTACAAGACCACGC
CTCCCGTGCTGGACTCCGACGGCTCCTTCTTCCTCTACAGCAAGCTCACCGTGGACA
AGAGCAGGTGGCAGCAGGGGAACGTCTTCTCATGCTCCGTGATGCATGAGGCTCTG
CACAACCACTACACGCAGAAGAGCCTCTCCCTGTCTCCGGGTAAATGA

FIG. 17A

B  V$_H$4-hIgG1C$_H$ Amino acid sequence
AATMGWSWILLFLLSVTAGVHSQVQLQESGPGLVKPSETLSLTCTVSGFSISRYSVHWIR
QPPGKGLEWIGLIWGGGFTDYNSALKSRVTISKDNSKNQVSLKLSSVTAADTAVYYCAR
EGVAYWGQGTLVTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKKVEPKSC
DKTHTCPPCPAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALPAPIEKTIS
KAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPGK*

FIG. 17B

A V$_H$6-hIgG1C$_H$ DNA sequence

GCCGCCACCATGGGCTGGAGCTGGATCCTGCTGTTCCTCCTGAGCGTGACAGCAGGA
GTGCACAGCCAAGTCCAACTGCAAGAAAGTGGTCCGGGCCTGGTGAAACCGAGTGA
AACCCTGTCTCTGACGTGTACCGTGAGTGGCTTTAGCCTGAGCCGTTATAGCGTTCA
TTGGATTCGCCAGCCGCCGGGTAAAGGCCTGGAATGGATTGGTCTGATCTGGGGCG
GTGGCTTTACCGATTATAACAGCGCGCTGAAAAGCCGTGTGACCATCAGCAAAGAT
AACAGCAAAAATCAGGTGAGCCTGAAACTGAGCAGCGTTACCGCGGCCGATACCGC
CGTGTATTATTGCGCTCGTGAAGGCGTCGCTTACTGGGGCCAAGGCACCCTGGTTAC
CGTCTCCTCCGCTAGCACCAAGGGCCCATCGGTCTTCCCCCTGGCACCCTCCTCCAA
GAGCACCTCTGGGGGCACAGCGGCCCTGGGCTGCCTGGTCAAGGACTACTTCCCCG
AACCGGTGACGGTGTCGTGGAACTCAGGCGCCCTGACCAGCGGCGTGCACACCTTC
CCGGCTGTCCTACAGTCCTCAGGACTCTACTCCCTCAGCAGCGTGGTGACCGTGCCC
TCCAGCAGCTTGGGCACCCAGACCTACATCTGCAACGTGAATCACAAGCCCAGCAA
CACCAAGGTGGACAAGAAAGTTGAGCCCAAATCTTGTGACAAAACTCACACATGCC
CACCGTGCCCAGCACCTGAACTCCTGGGGGGACCGTCAGTCTTCCTCTTCCCCCCAA
AACCCAAGGACACCCTCATGATCTCCCGGACCCCTGAGGTCACATGCGTGGTGGTG
GACGTGAGCCACGAAGACCCTGAGGTCAAGTTCAACTGGTACGTGGACGGCGTGGA
GGTGCATAATGCCAAGACAAAGCCGCGGGAGGAGCAGTACAACAGCACGTACCGT
GTGGTCAGCGTCCTCACCGTCCTGCACCAGGACTGGCTGAATGGCAAGGAGTACAA
GTGCAAGGTCTCCAACAAAGCCCTCCCAGCCCCCATCGAGAAAACCATCTCCAAAG
CCAAAGGGCAGCCCCGAGAACCACAGGTGTACACCCTGCCCCCATCCCGGGATGAG
CTGACCAAGAACCAGGTCAGCCTGACCTGCCTGGTCAAAGGCTTCTATCCCAGCGAC
ATCGCCGTGGAGTGGGAGAGCAATGGGCAGCCGGAGAACAACTACAAGACCACGC
CTCCCGTGCTGGACTCCGACGGCTCCTTCTTCCTCTACAGCAAGCTCACCGTGGACA
AGAGCAGGTGGCAGCAGGGGAACGTCTTCTCATGCTCCGTGATGCATGAGGCTCTG
CACAACCACTACACGCAGAAGAGCCTCTCCCTGTCTCCGGGTAAATGA

FIG. 18A

B V$_H$6-hIgG1C$_H$ Amino acid sequence

AATMGWSWILLFLLSVTAGVHSQVQLQESGPGLVKPSETLSLTCTVSGFSLSRYSVHWI
RQPPGKGLEWIGLIWGGGFTDYNSALKSRVTISKDNSKNQVSLKLSSVTAADTAVYYCA
REGVAYWGQGTLVTVSSASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKKVEPKS
CDKTHTCPPCPAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALPAPIEKTIS
KAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPGK*

FIG. 18B

A $V_L$-hIgG1$C_H$ DNA sequence
GCCGCCACCATGGGCTGGAGCTGGATCCTGCTGTTCCTCCTGAGCGTGACAGCAGGA
GTGCACAGCGATGTCGTGATGACGCAATCCCCGCTGTCGCTGCCGGTGACGCTGGGC
CAACCGGCAAGCATTTCGTGTAAAAGCTCGCAAAGCCTGCTGAACAGCGATGGTCG
TACCTATCTGAATTGGTTTCAGCAGCGTCCGGGTCAGAGCCCGCGTCGTCTGATTTA
TCTGGTGAGCAAACTGGATAGCGGTGTTCCGGATCGTTTTAGCGGCAGCGGTAGCGG
CACCGATTTTACCCTGAAAATCAGCCGCGTGGAAGCGGAAGATGTGGGCGTTTATTA
TTGCTGGCAGGGCACCCATTTTCCGTTCACCTTCGGTCCGGGCACCAAAGTTGACAT
TAAACGAACGGTGGCTGCACCATCTGTCTTCATCTTCCCGCCATCTGATGAGCAGTT
GAAATCTGGAACTGCCTCTGTTGTGTGCCTGCTGAATAACTTCTATCCCAGAGAGGC
CAAAGTACAGTGGAAGGTGGATAACGCCCTCCAATCGGGTAACTCCCAGGAGAGTG
TCACAGAGCAGGACAGCAAGGACAGCACCTACAGCCTCAGCAGCACCCTGACGCTG
AGCAAAGCAGACTACGAGAAACACAAAGTCTACGCCTGCGAAGTCACCCATCAGGG
CCTGAGCTCGCCCGTCACAAAGAGCTTCAACAGGGGAGAGTGTTAG

FIG. 19A

B $V_L$-hIgK$C_H$ Amino acid sequence
AATMGWSWILLFLLSVTAGVHSDVVMTQSPLSLPVTLGQPASISCKSSQSLLNSDGRTY
LNWFQQRPGQSPRRLIYLVSKLDSGVPDRFSGSGSGTDFTLKISRVEAEDVGVYYCWQG
THFPFTFGPGTKVDIKRTVAAPSVFIFPPSDEQLKSGTASVVCLLNNFYPREAKVQWKVD
NALQSGNSQESVTEQDSKDSTYSLSSTLTLSKADYEKHKVYACEVTHQGLSSPVTKSFN
RGEC*

FIG. 19B

CD6 ANTIBODY FOR TREATMENT OF T-CELL MEDIATED DISEASES OR DISORDERS

CROSS-REFERENCE TO RELATED APPLICATIONS

This application is a continuation of U.S. patent application Ser. No. 15/623,729, filed on Jun. 15, 2017, which claims the benefit of U.S. Provisional Application Ser. No. 62/350,218, filed on Jun. 15, 2016. This application incorporates the above-identified applications herein by reference in their entirety.

GOVERNMENT FUNDING

This invention was made with government support under NS081443 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jun. 8, 2017, is named CCF-024421USORD_SL.txt and is 37,492 bytes in size.

BACKGROUND

CD6 is primarily expressed on T cells. Kamoun et al., J Immunol 127: 987-991 (1981). Results from previous in vitro studies using different CD6-specific monoclonal antibodies (mAbs) are contradictory, suggesting that CD6 can either stimulate or suppress T-cell activation. Bott et al., Int Immunol 5: 783-792 (1993); Singer et al., Immunology 88: 537-543 (1996). CD6 has also long been proposed as a potential target for therapy of autoimmune diseases, and despite the lack of clear understanding of CD6's function, recently a humanized mAb against CD6 has been approved for treating psoriasis in India. Jayaraman, K., Nature Biotechnology 31: 1062-1063 (2013). However, historically, in the United States, the first wave of programs aimed at using CD6-targeted reagents in treating human diseases was dropped or slowed, due in part to the lack of in vivo data to confirm the in vitro and ex vivo studies and to the absence of CD6 gene engineered animals to test CD6-targeted reagents in vivo. Pinto, M. & Carmo, A. M., BioDrugs: clinical immunotherapeutics, biopharmaceuticals and gene therapy 27: 191-202 (2013). So far, there is only one report on in vivo studies of CD6 using genetically engineered animals (Orta-Mascaró, M. et al. J Exp Med 213(8): 1387-1397 (2016)), and the potential role of CD6 in multiple sclerosis (MS) remains elusive. Recent genomic wide association studies from several groups identified CD6 as a risk gene for MS (De Jager et al., Nat Genet 41: 776-782 (2009); Heap et al., Hum Mol Genet 19: 122-134 (2010)), arguing a significant role of CD6 in the pathogenesis of MS.

SUMMARY OF THE INVENTION

In one aspect, the present invention provides a method of treating a T-cell mediated disease or disorder in a subject by administering to the subject a therapeutically effective amount of an antibody or fragment thereof that specifically binds to CD6. In some embodiments, the disease or disorder is an autoimmune disease or transplant rejection. In further embodiments, the T-cell mediated disease is multiple sclerosis.

A variety of antibodies or fragment thereof that specifically binds to CD6 can be used to treat the T-cell mediated disease or disorder. In some embodiments, the antibody is a monoclonal antibody. In other embodiments, particular if the subject is human, the antibody is a humanized antibody. In further embodiments, the humanized antibody is selected from the group of antibodies consisting of Fab2, Fab4, and Fab6, or variants thereof including only conservative sequence modifications.

Another aspect of the present invention provides a humanized antibody or antigen-binding fragment thereof having binding specificity for CD6, wherein the antibody selected from the group of antibodies consisting of Fab2, Fab4, and Fab6, or variants thereof including only conservative sequence modifications. In some embodiments, the humanized antibody comprises a heavy chain comprising SEQ ID NO: 1, a light chain comprising SEQ ID NO: 2, or variants thereof including only conservative sequence modifications. In other embodiments, the humanized antibody comprises a heavy chain comprising SEQ ID NO: 3, a light chain comprising SEQ ID NO: 4, or variants thereof including only conservative sequence modifications. In further embodiments, the humanized antibody comprises a heavy chain comprising SEQ ID NO: 5, a light chain comprising SEQ ID NO: 6, or variants thereof including only conservative sequence modifications.

Another aspect of the invention provides a kit comprising a humanized antibody or fragment thereof that specifically binds to CD6, and a package for holding the antibody. In some embodiments, the kit includes instructions for using the kit to carry out a method of treating a T-cell mediated disease or disorder in a subject by administering to the subject a therapeutically effective amount of the humanized antibody or fragment thereof that specifically binds to CD6. In additional embodiments, the disease is an autoimmune disease such as multiple sclerosis. In yet further embodiments, the antibody is selected from the group of antibodies consisting of Fab2, Fab4, and Fab6, or variants thereof including only conservative sequence modifications.

BRIEF DESCRIPTION OF THE FIGURES

The present invention may be more readily understood by reference to the following figures, wherein:

FIGS. 1A-1C provide graphs and images showing the development of the CD6 KO mice. A. Exons 5-7 of the CD6-coding region were replaced by a neomycin gene cassette after homologous recombination. Southern blot confirmed the recombination event. B. CD6 KO mice genotyping. All mCD6 KO mice were genotyped with a dual PCR. The neo insert can be identified by a PCR with a neo primer (forward-5'-CTT GGG TGG AGA GGC TAT TC-3') (SEQ ID NO: 7) and a exon 8 (reverse-5'-AGC CAA CCT TTC TTC TGA GAG CCA-3') (SEQ ID NO: 8). Mice heterozygous for the neo insert will also contain mouse CD6 exon 5 (forward-5'-TGG GCC CAA AGC ATT TAG CTT GAC-3') (SEQ ID NO: 9) and (reverse-5'-TAC AGA GAG CTT GGC AGT GCT TGA-3') (SEQ ID NO: 10). A mouse containing neo between exons 5-7 (lane 1) but also having exon 5 (lane 5) is a heterozygous KO. In contrast, a homologous KO has neo (lane 2) but does not contain exon 5 (lane 6). Lane 3 is the 100 base pair ladder and lane 4 is a PCR negative control. C. Absence of CD6 protein on CD6 KO mouse lymphocytes. Lymphocytes from WT, heterozygous (Het) KO and homologous (homo) KO mice were analyzed for CD6 expression by flow cytometry, showing reduced levels of CD6 in het KO mice (middle dotted line), and absence of CD6 in homo KO mice (left solid line). Neg, negative control.

FIGS. 2A-2E provide graphs and images showing that CD6 KO mice are protected from EAE. A. Clinical scores of the WT (circles) and CD6 KO mice (squares). Combined results from four experiments. n=15 in each group. $*p<0.01$; B. MOG-specific Th1 and Th17 responses were reduced in CD6 KO mice ($*p<0.05$). Splenocytes from WT and CD6 KO mice 21 days after immunization were incubated without peptide (white bars), with 10 μg/mL of nonrelevant peptide (IRBP$_{1-20}$, gray bars) or with 10 μg/mL MOG$_{79-96}$ peptide (black bars) for 72 hours. IFN-γ and IL-17 levels in the culture supernatants were measured by ELISA (n=14 in each group, $*p<0.05$). C. Spinal cord in CD6 KO mice had markedly reduced leukocyte infiltration as assessed by H&E staining. D. Representative images of spinal cord sections from the EAE mice after H&E staining, showing that CD6 KO mice have significantly reduced cell infiltration. (Magnification: Upper, 4×; Insets shown at Lower, 20×). E. Representative images of spinal cord sections from the EAE mice after Luxol Blue staining, showing that CD6 KO mice had intact myelin sheath (blue staining) compared with severe demyelination in the WT mice. (Magnification: 4×).

FIGS. 4A-4B provide graphs showing that absence of CD6 leads to augmented T cell activation. Purified CD4+ T cells from naïve WT and CD6 KO mice were activated by incubation with 1 μg/mL anti-CD3 and anti-CD28 mAbs, then the activation of cells was assessed 5 hours later by measuring the up-regulation of activation markers CD25 (A) and CD69 (B) using flow cytometric analysis. Gray bars, before activation; black bars, 5 hours after activation, n=5, data are mean±SEM, $*p<0.05$.

FIGS. 5A-5D provide graphs showing that absence of CD6 leads to reduced proliferation and enhanced apoptosis of activated T cells. Purified CD4+ T cells from naïve WT and CD6 KO mice were activated by incubation with plate-bound anti-CD3 and anti-CD28 mAbs, then cultured under the Th1 or Th17 polarization conditions. At 5, 24, 48, and 72 hour time points, proliferation of the activated cells was assessed by measuring BrdU incorporation using a BrdU ELISA kit (A and B), and apoptosis of the activated T cells was assessed by staining the cells with annexin V followed by flow cytometric analysis (C and D). n=3 in each group, data are mean±SEM, $*p<0.05$.

FIGS. 6A-6C provide graphs and images showing the absence of CD6 reduces T-cell migration through BMEC monolayers. WT DBA-1 mouse BMECs were first isolated by following an established protocol (A) and were ~90% pure based on CD34 staining (B). The isolated BMECs were grown on culture inserts until monolayers were formed, then 0.6×10$^6$ of CFSE-labeled and anti-CD3/CD28 mAb-activated T cells from naïve WT and CD6 KO mice were added into the culture inserts with 20 ng/mL culture, cells that remained in the culture inserts and those that migrated into the lower chambers were quantitated (C). n=4 in each group, data are mean±SEM, $*pp<0.05$.

FIGS. 7A-7G provide graphs and images showing that mouse anti-human CD6 mAb (UMCD6) treats EAE in CD6 humanized mice. A and B. CD6 humanized mice do not express mouse CD6 (A) but express human CD6 (B). C. EAE clinical scores of CD6 humanized mice treated with UMCD6 and control mouse IgGs. CD6 humanized mice were immunized to induced EAE. After mice showed mild clinical symptoms they were randomly divided into two groups with one group receiving ~0.4 mg per mouse anti-human CD6 IgG (UMCD6) (circles) and the other receiving 0.4 mg purified mouse IgGs (squares). Clinical scores were recorded daily. n=14 in each group, $*p<0.05$. D and E. Th1 (D) and Th17 (E) recall assays in CD6 humanized mice treated with UMCD6 or control IgG. At the end of treatment experiments (day 14), splenocytes from mice were collected and incubated without peptide (light gray bars), with 10 μg/mL of a nonrelevant peptide (IRBP$_{1-20}$, dark gray bars) or with 10 μg/mL MOG$_{79-96}$ peptide (black bars) for 72 hours. IFN-γ and IL-17a levels in the culture supernatants were measured by ELISA. n=7 in each group, $*p<0.05$. F and G. Representative images of spinal cord sections showing significantly reduced cell infiltration (F) and demyelination (G) in the UMCD6-treated mice compared with the controls. (Magnification: 4×).

FIGS. 8A-8B provide graphs and images showing that UMCD6 treatment does not deplete T cells. CD4+ and CD8+ T cell percentages in the peripheral blood were analyzed in both UMCD6 and control IgG-treated CD6 humanized mice by flow cytometry at the end of the treatment studies, showing no difference between the two groups of mice. n=14 in each group. A. FSC/SSC shows the lymphocyte population analyzed. B. CD4+ and CD8+ T cell percentages of mice treated with UMCD6 (black bars) or control IgG (gray bars).

FIGS. 16A and 16B provide the (A) DNA (SEQ ID NO: 18) and (B) amino acid sequences (SEQ ID NO: 19) for the $V_H2$-hIgG1$C_H$ antibody fragment.

FIGS. 17A and 17B provide the (A) DNA (SEQ ID NO: 20) and (B) amino acid sequences (SEQ ID NO: 21) for the $V_H4$-hIgG1$C_H$ antibody fragment.

FIGS. 18A and 18B provide the (A) DNA (SEQ ID NO: 22) and (B) amino acid sequences (SEQ ID NO: 23) for the $V_H4$-hIgG1$C_H$ antibody fragment.

FIGS. 19A and 19B provide the (A) DNA (SEQ ID NO: 24) and (B) amino acid sequences (SEQ ID NO: 25) for the $V_L$-hIgK$C_L$ antibody fragment.

DETAILED DESCRIPTION OF THE INVENTION

Figure 3A:
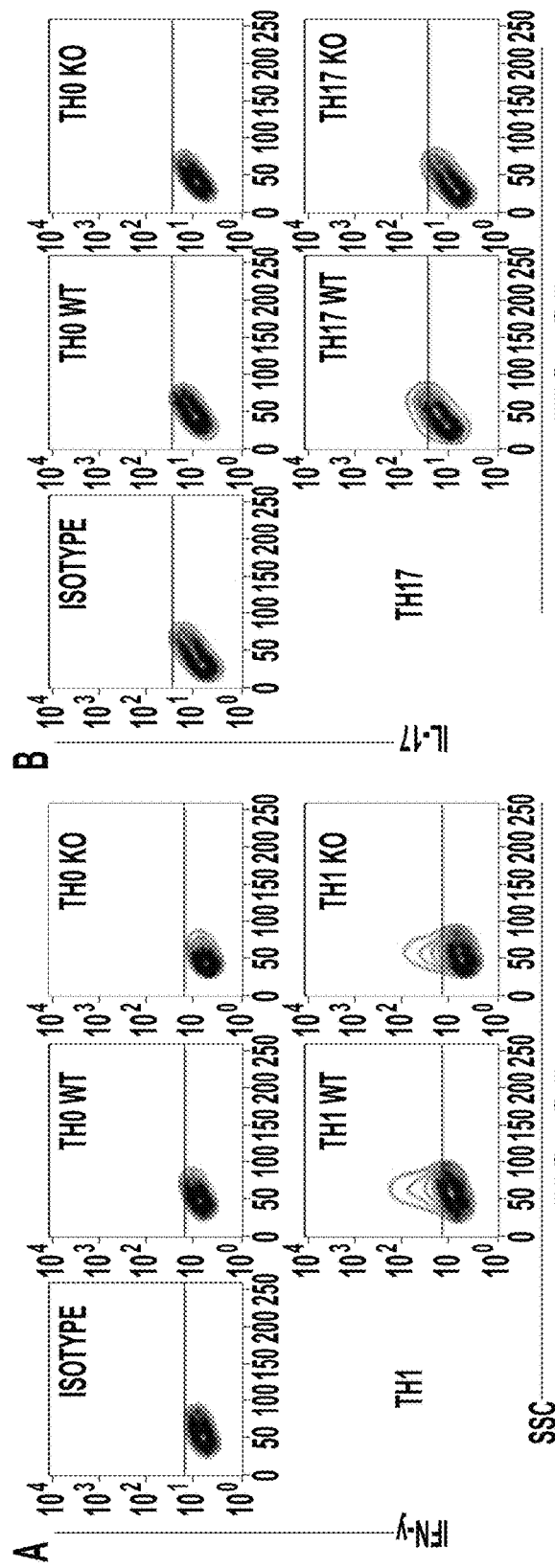
FIGS. 3A-3D provide graphs and images showing that absence of CD6 leads to impaired Th1 and Th17 development. Purified CD4+ T cells from naïve WT and CD6 KO mice were activated and cultured under Th1 or Th17 polarization conditions for 5 days. Then the development of Th1 and Th17 was assessed by intracellular staining of IFN-γ or IL-17a. A and B. Representative results of the intracellular IFN-γ or IL-17a staining within the differentiated T cells. C and D. Combined results from three different experiments. n=3, data are mean±SEM, $*p<0.05$.
Figure 3B:
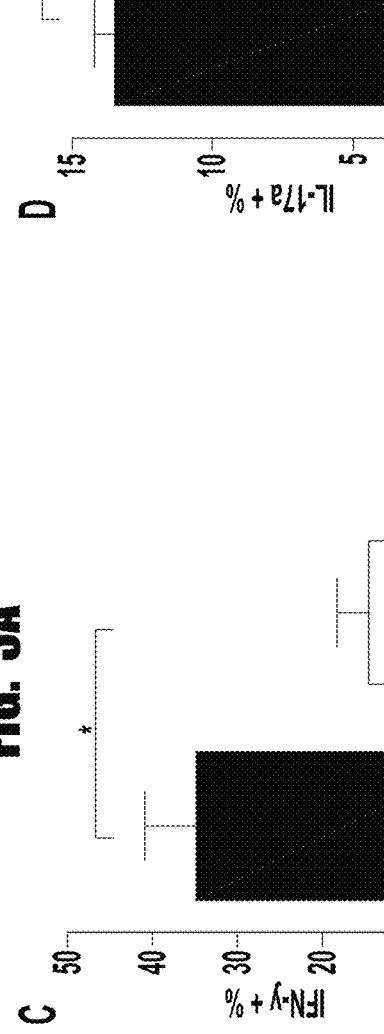
Figure 3C:
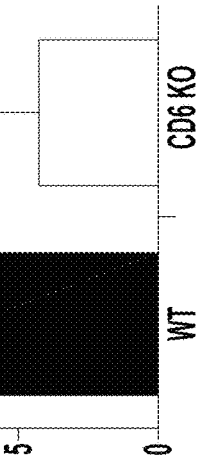
Figure 3D:
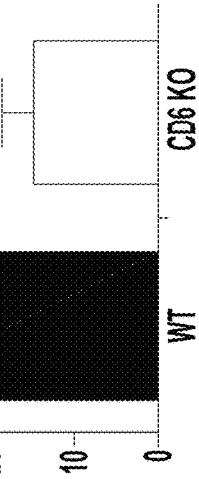

Unless otherwise defined, all technical and scientific terms used herein have the same meaning as commonly understood by one of ordinary skill in the art to which these exemplary embodiments belong. The terminology used in the description herein is for describing particular exemplary embodiments only and is not intended to be limiting of the exemplary embodiments. As used in the specification and the appended claims, the singular forms "a," "an," and "the" are intended to include the plural forms as well, unless the context clearly indicates otherwise. All publications, patent applications, patents, and other references mentioned herein are incorporated by reference in their entirety.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present embodiments. At the very least, and not as an attempt to limit the application of the doctrine of equivalents to the scope of the claims, each numerical parameter should be construed in light of the number of significant digits and ordinary rounding approaches.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

"Treating", as used herein, means ameliorating the effects of, or delaying, halting or reversing the progress of a disease or disorder. The word encompasses reducing the severity of a symptom of a disease or disorder and/or the frequency of a symptom of a disease or disorder.

A "subject", as used therein, can be a human or non-human animal. Non-human animals include, for example, livestock and pets, such as ovine, bovine, porcine, canine, feline and murine mammals, as well as reptiles, birds and fish. Preferably, the subject is human.

The language "effective amount" or "therapeutically effective amount" refers to a nontoxic but sufficient amount of the composition used in the practice of the invention that is effective to provide effective treatment in a subject. That result can be reduction and/or alleviation of the signs, symptoms, or causes of a disease or disorder, or any other desired alteration of a biological system. An appropriate therapeutic amount in any individual case may be determined by one of ordinary skill in the art using routine experimentation.

The term antibody, as used herein and unless further limited, refers to single chain, two-chain, and multi-chain proteins and glycoproteins belonging to the classes of polyclonal, monoclonal, chimeric and hetero immunoglobulins; it also includes synthetic and genetically engineered variants of these immunoglobulins. The term "Antibody fragment" includes Fab, Fab', F(ab')2, and Fv fragments, as well as any portion of an antibody having specificity toward a desired target epitope or epitopes.

The term monoclonal antibody, as used herein, refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different epitopes, each monoclonal antibody is directed against a single epitope on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies.

The term chimeric antibody, as used herein, refers to an antibody which includes sequences derived from two different antibodies, which typically are of different species. Most typically, chimeric antibodies include human and non-human antibody fragments, generally human constant and non-human variable regions.

The term humanized antibody, as used herein, refers to a type of chimeric antibody derived from a non-human antibody, and a human antibody which retains or substantially retains the antigen-binding properties of the parent antibody but which is less immunogenic in humans.

The term antigen, as used herein, refers to a molecule or a portion of a molecule capable of being bound by an antibody which is additionally capable of inducing an animal to produce an antibody capable of binding to an epitope of that antigen. An antigen can have one or more than one epitope. The specific reaction referred to above is meant to indicate that the antigen will react, in a highly selective manner, with its corresponding antibody and not with the multitude of other antibodies which can be evoked by other antigens.

The term epitope, as used herein, refers to that portion of any molecule capable of being recognized by, and bound by, an antibody. In general, epitopes consist of chemically active surface groupings of molecules, for example, amino acids or sugar side chains, and have specific three-dimensional structural characteristics as well as specific charge characteristics. The epitopes of interest for the present invention are epitopes comprising amino acids.

As used herein, a humanized antibody comprises heavy or light chain variable framework regions that are "the product of" or "derived from" a particular human germline sequence (human gene) if the variable framework regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A humanized antibody which comprises a heavy or light chain variable framework region that is "the product of" or "derived from" a human germline immunoglobulin sequence can be identified as such by comparing the amino acid sequence of the heavy or light chain variable framework region of the humanized antibody to the amino acid sequences of the heavy or light chain variable framework region of human germline immunoglobulins. A humanized antibody that comprises a heavy or light chain variable framework region that is "the product of" a particular human germline immunoglobulin sequence has a heavy or light chain variable framework region which is 100% identical in amino acid sequence to the heavy or light chain variable framework region of the particular human germline immunoglobulin sequence. A humanized antibody that comprises a heavy or light chain variable framework region that is "derived from" a particular human germline immunoglobulin sequence may contain amino acid differences as compared to the heavy or light chain variable framework region of the particular germline sequence, due to, for example, naturally-occurring somatic mutations or intentional introduction of site-directed mutation. However, a selected humanized antibody typically is at least 90% identical in amino acid sequence of the heavy or light chain variable framework region to an amino acid sequence encoded by the heavy or light chain variable framework region of a human germline immunoglobulin gene and contains amino acid residues that identify the humanized antibody as being derived from human when compared to the germline immunoglobulin amino acid sequences of other species (e.g., murine germline sequences). In certain cases, a humanized antibody may be preferably at least 95%, more preferably at least 96%, most preferably at least 97%, in particular at least 98%, most particular at least 99%, identical in amino acid sequence of the heavy or light chain variable framework region to the amino acid sequence of the heavy or light chain variable framework region encoded by the germline immunoglobulin gene. Typically, the heavy or light chain variable framework region of a humanized antibody derived from a particular human germline sequence will display no more than 10 amino acid, preferably no more than 5, or even more preferably no more than 4, 3, 2, or 1 differences from the amino acid sequence of the heavy or light chain variable framework region encoded by the human germline immunoglobulin gene.

The term "Fab" or "Fab region" as used herein includes the polypeptides that comprise the VH, CH1, VL, and CL immunoglobulin domains. Fab may refer to this region in isolation, or this region in the context of a full length antibody or antibody fragment.

The term "Fc" or "Fc region", as used herein includes the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains.

The term "variant antibody" or "antibody variant" as used herein includes an antibody sequence that differs from that of a parent antibody sequence by virtue of at least one amino acid modification compared to the parent. The variant antibody sequence herein will preferably possess at least about 80%, most preferably at least about 90%, more preferably at least about 95% amino acid sequence identity with a parent antibody sequence. Antibody variant may refer to the antibody itself, compositions comprising the antibody variant, or the amino acid sequence that encodes it.

Antibody fragments include, but are not limited to, (i) the Fab fragment consisting of VL, VH, CL and CH1 domains, including Fab' and Fab'-SH, (ii) the Fd fragment consisting of the VH and CH1 domains, (iii) the Fv fragment consisting of the VL and VH domains of a single antibody; (iv) the dAb fragment (Ward et al., Nature 341:544-546 (1989)) which consists of a single variable, (v) F(ab')2 fragments, a bivalent fragment comprising two linked Fab fragments (vi) single chain Fv molecules (scFv), wherein a VH domain and a VL domain are linked by a peptide linker which allows the two domains to associate to form an antigen binding site (Bird et al., Science 242:423-426 (1988); Huston et al., Proc. Natl. Acad. Sci. U.S.A. 85:5879-5883 (1988)), (vii) bispecific single chain Fv dimers (PCT/US92/09965), (viii) "diabodies" or "triabodies", multivalent or multi-specific fragments constructed by gene fusion (Tomlinson et. al., Methods Enzymol. 326:461-479 (2000); WO94/13804; Holliger et al., Proc. Natl. Acad. Sci. U.S.A. 90:6444-6448 (1993)) and (ix) scFv genetically fused to the same or a different antibody (Coloma & Morrison, Nature Biotechnology 15, 159-163 (1997)).

Antibodies are grouped into classes, also referred to as isotypes, as determined genetically by the constant region. Human constant light chains are classified as kappa (CK) and lambda (CX) light chains. Heavy chains are classified as mu, delta, gamma, alpha, or epsilon, and define the antibody's isotype as IgM, IgD, IgG, IgA, and IgE, respectively. The IgG class is the most commonly used for therapeutic purposes. In humans this class comprises subclasses IgG1, IgG2, IgG3, and IgG4. In mice this class comprises subclasses IgG1, IgG2a, IgG2b, IgG3. IgM has subclasses, including, but not limited to, IgM1 and IgM2. IgA has several subclasses, including but not limited to IgA1 and IgA2. Thus, "isotype" as used herein is meant any of the classes or subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE.

As used herein, an antibody "specifically binds", referring to an antibody binding to a target structure, means that the antibody binds a target structure, or subunit thereof, but does not bind to a biological molecule that is not a target structure. Antibodies that specifically bind to a target structure, or subunit thereof, do not cross-react with biological molecules that are outside the target structure family. An antibody specific for CD6 can be an antibody or antibody fragment capable of binding to that specific protein with a specific affinity of between $10^{-8}$ M and $10^{-11}$ M. In some embodiments, an antibody or antibody fragment binds to a selected antigen with a specific affinity of greater than $10^{-7}$ M, $10^{-8}$ M, $10^{-9}$ M, $10^{-10}$ M, or $10^{-11}$ M, between $10^{-8}$ M-$10^{-11}$ M, $10^{-9}$ M-$10^{-10}$ M, and $10^{-10}$ M-$10^{-11}$ M. In a preferred aspect, specific activity is measured using a competitive binding assay as set forth in Ausubel FM, (1994). Current Protocols in Molecular Biology. Chichester: John Wiley and Sons ("Ausubel"), which is incorporated herein by reference.

The term "amino acid modification" herein includes an amino acid substitution, insertion, and/or deletion in a polypeptide sequence. By "amino acid substitution" or "substitution" herein is meant the replacement of an amino acid at a particular position in a parent polypeptide sequence with another amino acid. For example, the substitution R94K refers to a variant polypeptide, in this case a heavy chain variable framework region variant, in which the arginine at position 94 is replaced with a lysine. For the preceding example, 94K indicates the substitution of position 94 with a lysine. For the purposes herein, multiple substitutions are typically separated by a slash. For example, R94K/L78V refers to a double variant comprising the substitutions R94K and L78V. By "amino acid insertion" or "insertion" as used herein is meant the addition of an amino acid at a particular position in a parent polypeptide sequence. For example, insert −94 designates an insertion at position 94. By "amino acid deletion" or "deletion" as used herein is meant the removal of an amino acid at a particular position in a parent polypeptide sequence. For example, R94- designates the deletion of arginine at position 94.

As used herein, the term "conservative modifications" or "conservative sequence modifications" is intended to refer to amino acid modifications that do not significantly affect or alter the binding characteristics of the antibody containing the amino acid sequence. Such conservative modifications include amino acid substitutions, insertions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the constant or variable regions of an antibody of the invention can be replaced with other amino acid residues from the same side chain family and the altered antibody (variant antibody) can be tested for retained function.

Methods of Treating T-Cell Mediated Disease

In one aspect, the present invention provides a method of treating a T-cell mediated disease or disorder in a subject by administering to the subject a therapeutically effective amount of an antibody or fragment thereof that specifically binds to CD6.

In some embodiments of the invention, the T-cell mediated disease or disorder is an autoimmune disease. Examples of T-cell mediated autoimmune diseases include multiple sclerosis, polymyositis, acute disseminated encephalomyelitis, Balo's disease, clinically isolated syndrome, HTLV-I associated myelopathy, neuromyelitis optica, Schilder's disease, and transverse myelitis. In other embodiments, the T-cell mediated disease or disorder is transplantation rejection. In transplant rejection, transplanted tissue is rejected by the recipient's immune system, which damages or destroys the transplanted tissue. Alloreactive killer T cells, also called cytotoxic T lymphocytes (CTLs), have CD8 receptors that dock to the transplanted tissue's MHC class I molecules, which display the donor's self peptides, and trigger the target cell's programmed cell death by apoptosis. T-cell mediated transplant rejection is typically acute rejection.

In some embodiments, the T-cell mediated disease or disorder is multiple sclerosis. Multiple sclerosis is an inflammatory disease in which the insulating covers of nerve cells in the brain and spinal cord are damaged. This damage disrupts the ability of parts of the nervous system to communicate. Specific symptoms of multiple sclerosis are determined by the locations of the lesions within the nervous system, and may include loss of sensitivity or changes in sensation such as tingling, pins and needles or numbness, muscle weakness, very pronounced reflexes, muscle spasms, or difficulty in moving; difficulties with coordination and balance (ataxia); problems with speech or swallowing, visual problems (nystagmus, optic neuritis or double vision), feeling tired, acute or chronic pain, and bladder and bowel difficulties, among others.

The antibody (e.g., humanized immunoglobulin) is administered in an effective amount which inhibits binding of CD6 to a ligand thereof. For therapy, an effective amount will be sufficient to achieve the desired therapeutic (including prophylactic) effect (such as an amount sufficient to reduce or prevent CD6-mediated binding and/or signalling). The antibody can be administered in a single dose or multiple doses. The dosage can be determined by methods known in the art and can be dependent, for example, upon the individual's age, sensitivity, tolerance and overall well-being. Suitable dosages for antibodies can be from about 0.1 mg/kg body weight to about 10.0 mg/kg body weight per treatment.

According to the method, the antibody (e.g., humanized immunoglobulin) can be administered to an individual (e.g., a human) alone or in conjunction with another agent. A humanized immunoglobulin can be administered before, along with or subsequent to administration of the additional agent. Thus, the invention includes pharmaceutical compositions comprising an anti-CD6 antibody or fragment thereof of the invention and a suitable carrier. In one embodiment, more than one anti-CD6 antibody which inhibits the binding of CD6 to its ligand(s) is administered. In another embodiment, an additional pharmacologically active ingredient (e.g., an agent suitable for treating multiple sclerosis, such as an interferon, fingolimod, teriflunomide, dimethyl fumarate, glatiramer acetate, methotrexate, or natalizumab) can be administered in conjunction with an anti-CD6 antibody of the present invention. A variety of routes of administration are possible, including, but not necessarily limited to, parenteral (e.g., intravenous, intraarterial, intramuscular, subcutaneous injection), oral (e.g., dietary), topical, inhalation (e.g., intrabronchial, intranasal or oral inhalation, intranasal drops), or rectal, depending on the disease or condition to be treated. Parenteral administration is a preferred mode of administration.

Formulation will vary according to the route of administration selected (e.g., solution, emulsion). An appropriate composition comprising the anti-CD6 antibody to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See, generally, Remington's Pharmaceutical Sciences, 17th Edition, Mack Publishing Co., PA, 1985). For inhalation, the compound can be solubilized and loaded into a suitable dispenser for administration (e.g., an atomizer, nebulizer or pressurized aerosol dispenser).

The antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml. Alternatively, antibody can be administered as a sustained release formulation, in which case less frequent administration is required. Dosage and frequency vary depending on the half-life of the antibody in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated.

The selected dosage level will depend upon a variety of pharmacokinetic factors including the activity of the particular compositions of the present invention employed, the route of administration, the time of administration, the rate of excretion of the particular antibody being employed, the duration of the treatment, other drugs, compounds and/or materials used in combination with the particular compositions employed, the age, sex, weight, condition, general health and prior medical history of the patient being treated, and like factors well known in the medical arts.

CD6 Antibodies

The present invention involves administering a therapeutically effective amount of an antibody or fragment thereof that specifically binds to CD6 to a subject. CD6 (Cluster of Differentiation 6) is a human protein encoded by the CD6 gene, found on the outer membrane of T-lymphocytes as well as some other immune cells. The encoded protein contains three scavenger receptor cysteine-rich (SRCR) domains and a binding site for an activated leukocyte cell adhesion molecule. In some embodiments, the antibody is a monoclonal antibody. Preparation of immunizing antigen, and polyclonal and monoclonal antibody production can be performed as described herein, or using other suitable techniques. A variety of methods have been described (see e.g., Kohler et al., Nature, 256: 495-497 (1975) and Eur. J. Immunol. 6: 511-519 (1976); Milstein et al., Nature 266: 550-552 (1977); Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); Current Protocols In Molecular Biology, Vol. 2 (Supplement 27, Summer '94), Ausubel, F. M. et al., Eds., (John Wiley & Sons: New York, N.Y.), Chapter 11, (1991)). Generally, a hybridoma can be produced by fusing a suitable immortal cell line (e.g., a myeloma cell line such as SP2/0) with antibody producing cells. The antibody producing cell, preferably those of the spleen or lymph nodes, are obtained from animals immunized with the antigen of interest. The fused cells (hybridomas) can be isolated using selective culture conditions, and cloned by limiting dilution. Cells which produce antibodies with the desired binding properties can be selected by a suitable assay (e.g., ELISA).

In some embodiments, the anti-CD6 antibody is a humanized antibody. Humanized antibodies are preferable for use in human subjects, in order to avoid generating an immune response against the antibodies themselves. Examples of humanized antibodies include those selected from the group of antibodies consisting of Fab2, Fab4, and Fab6, or variants thereof including only conservative sequence modifications. Other examples of humanized antibodies include those prepared by the inventors, as described herein.

In some embodiments, the humanized antibody comprises a heavy chain comprising the amino acid sequence QVQLQESGPGLVKP-SETLSLTCTVSGFSLSRYSVHWVRQPPGKGLEWLG-LIWGGGFTDY NSALKSRLTISKDNSKNQVSLKLSSVTAADTAVYY-CAREGVAYWGQGTLVTVSS (SEQ ID NO: 1), a light chain comprising the amino acid sequence DVVMTQSPLSLPVTLGQPASISCK-SSQSLLNSDGRTYLNWFQQRPGQSPRRLIYLVSKLD SGVPDRFSGSGSGTDFTLKISRVEAE-DVGVYYCWQGTHFPFTFGPGTKVDIK (SEQ ID NO: 2), or variants thereof including only conservative sequence modifications.

In some embodiments, the humanized antibody comprises a heavy chain comprising the amino acid sequence QVQLQESGPGLVKPSETLSLTCTVSGFSIS-RYSVHWIRQPPGKGLEWIGLIWGGGFTDYN SALKSRVTISKDNSKNQVSLKLSSVTAADTAVYY-CAREGVAYWGQGTLVTVSS (SEQ ID NO: 3), a light chain comprising the amino acid sequence DVVMTQSPLSLPVTLGQPASISCK-SSQSLLNSDGRTYLNWFQQRPGQSPRRLIYLVSKLD SGVPDRFSGSGSGTDFTLKISRVEAE-DVGVYYCWQGTHFPFTFGPGTKVDIK (SEQ ID NO: 4), or variants thereof including only conservative sequence modifications.

In some embodiments, the humanized antibody comprises a heavy chain comprising the amino acid sequence QVQLQESGPGLVKP-SETLSLTCTVSGFSLSRYSVHWIRQPPGKGLEWIG-LIWGGGFTDYN SALKSRVTISKDNSKNQVSLKLSSVTAADTAVYY-CAREGVAYWGQGTLVTVSS (SEQ ID NO: 5), a light chain comprising the amino acid sequence DVVMTQSPLSLPVTLGQPASISCK-SSQSLLNSDGRTYLNWFQQRPGQSPRRLIYLVSKLD SGVPDRFSGSGSGTDFTLKISRVEAE-DVGVYYCWQGTHFPFTFGPGTKVDIK (SEQ ID NO: 6), or variants thereof including only conservative sequence modifications.

Humanized immunoglobulins can be produced using synthetic and/or recombinant nucleic acids to prepare genes (e.g., cDNA) encoding the desired humanized chain. For example, nucleic acid (e.g., DNA) sequences coding for humanized variable regions can be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991)). Using these or other suitable methods, variants can also be readily produced. In one embodiment, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213).

The antigen binding region of the humanized immunoglobulin (the nonhuman portion) can be derived from an immunoglobulin of nonhuman origin (referred to as a donor immunoglobulin) having binding specificity for CD6. For example, a suitable antigen binding region can be derived from a murine monoclonal antibody having binding specificity for CD6. Other sources include CD6-specific antibodies obtained from nonhuman sources, such as rodent (e.g., mouse, rat), rabbit, pig goat or non-human primate (e.g., monkey). Additionally, other polyclonal or monoclonal antibodies, such as antibodies which bind to the same or similar epitope as the 1D9 antibody, can be made (e.g., Kohler et al., Nature, 256:495-497 (1975); Harlow et al., 1988, Antibodies: A Laboratory Manual, (Cold Spring Harbor, N.Y.); and Current Protocols in Molecular Biology, Vol. 2 (Supplement 27, Summer '94), Ausubel et al., Eds. (John Wiley & Sons: New York, N.Y.), Chapter 11 (1991)).

For example, antibodies can be raised against an appropriate immunogen in a suitable mammal (e.g., a mouse, rat, rabbit or sheep). Cells bearing CD6, membrane fractions containing CD6, and immunogenic fragments of CD6 are examples of suitable immunogens. Antibody-producing cells (e.g., a lymphocyte) can be isolated from, for example, the lymph nodes or spleen of an immunized animal. The cells can then be fused to a suitable immortalized cell (e.g., a myeloma cell line), thereby forming a hybridoma. Fused cells can be isolated employing selective culturing techniques. Cells which produce antibodies with the desired specificity can be selected by a suitable assay (e.g., ELISA). Immunoglobulins of nonhuman origin having binding specificity for CD6 can also be obtained from antibody libraries (e.g., a phage library comprising nonhuman Fab molecules).

Kits

Another aspect of the invention provides a kit comprising a humanized antibody or fragment thereof that specifically binds to CD6, and a package for holding the antibody. Suitable packages include, for example, bottles, vials or syringes. The package may be formed from a variety of materials such as glass or plastic. The container holds a composition that may be effective for treating the condition and may have a sterile access port (e.g., the container may be an intravenous solution bag or a vial having a stopper pierceable by a hypodermic injection needle). At least one active agent in the composition may be the anti-CD6 antibody described herein. The label or package insert may indicate that the composition may be used for treating the condition of choice, such as cancer. In one embodiment, the label or package insert may indicate that the composition comprising the anti-CD6 antibody may be used to treat a T-cell mediated disease or disorder.

The reagents may be supplied in a solid (e.g., lyophilized) or liquid form. The kits of the present invention may optionally comprise different containers (e.g., vial, ampoule, test tube, flask or bottle) for each individual buffer, cell type and/or reagent. Each component will generally be suitable as aliquoted in its respective container or provided in a concentrated form. Other containers suitable for conducting certain steps of the disclosed methods may also be provided. The individual containers of the kit are preferably maintained in close confinement for commercial sale. For example, the kit can include a carrier for the various components of the kit. The carrier can be a container or support in the form of, e.g., a bag, box, tube or rack, and is optionally compartmentalized. The carrier may define an enclosed container for safety purposes during shipment and storage.

The antibody or fragment thereof that specifically binds to CD6 can be any of the antibodies described herein. For example, in some embodiments the antibody is selected from the group of antibodies consisting of Fab2, Fab4, and Fab6, or variants thereof including only conservative sequence modifications.

In some embodiments, the kit further includes instructions for using the kit to carry out a method of treating a T-cell mediated disease or disorder in a subject by administering to the subject a therapeutically effective amount of the humanized antibody or fragment thereof that specifically binds to CD6. For example, in some embodiments, the kit includes instructions for carrying out a method of treating multiple sclerosis. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

Examples have been included to more clearly describe a particular embodiment of the invention and its associated cost and operational advantages. However, there are a wide variety of other embodiments within the scope of the present invention, which should not be limited to the particular examples provided herein.

EXAMPLES

Example 1: CD6 as a Target for Treatment of a Model of Multiple Sclerosis

CD6 has been recently identified as a risk gene for multiple sclerosis (MS), an autoimmune disease in which myelin-reactive T cells play important roles in pathogenesis. However, partially due to the lack of an animal model, the role of CD6 on regulating T cells is contradictory based on in vitro studies, and its potential as a new target for MS treatment remains unclear. Here, the generation of a CD6 knockout mouse and a CD6 humanized mouse is reported. It is demonstrated that (a) CD6 knockout mice are protected from central nervous system injuries in experimental autoimmune encephalomyelitis (EAE), an animal model of MS, (b) CD6 is a negative regulator of T cell activation, but a positive regulator of T cell proliferation and survival. Therefore, lack of CD6 leads to reduced T-cell responses in EAE; (c) CD6 on T cells is also required for T-cell infiltration through the blood-brain barrier (BBB) into the central nervous system (CNS), and (d) systemic administration of an anti-human CD6 antibody after disease onset reverses EAE progression in CD6 humanized mice. These data demonstrate that targeting CD6 should be effective in treating MS.

Methods

Development of the CD6 knockout (KO) mice: CD6 KO mice were developed following a conventional KO mice generation protocol. In this mouse, multiple exons including exons 5-7 of the CD6 gene were replaced by a neomycin cassette after homologous recombination, resulting in the absence of CD6 protein. The resultant CD6 KO mice were backcrossed with DBA-1 mice for 12 generations. As anticipated, flow cytometry showed that lymphocytes from the CD6 knockout mice are deficient in CD6 protein and these mice have the same numbers of CD4+ and CD8+ T cells compared with WT DBA-1 mice (FIG. 1).

Induction and assessment of disease severity of EAE: EAE was induced by active immunization, and disease severity was assessed by assigning clinical scores following previously published protocols. Li et al., Mol Immunol 46: 2885-2891 (2009). In brief, 8-10 weeks old female mice were immunized at base of tail and both thighs with 200 µg of mouse $MOG_{79-96}$ peptide (custom synthesized by Genscript, NJ) emulsified in Complete Freund's Adjuvant (CFA) (Sigma, MO) that had been supplemented with *M. tubercu-*

*losis* strain H37RA to 4 mg/ml. 0.2 μg of Pertussis toxin (List Biological Laboratories, CA) was injected i.p. right after immunization and the following day. Clinical severity was assessed daily with a 0 to 5 scoring system (0, no signs; 1, flaccid tail; 2, impaired righting reflex and/or gait; 3, partial hind limb paralysis; 4, total hind limb paralysis; 5, moribund or dead). Each mouse was assessed twice within the same day, and the average score from the two assessments was recorded as the score for that day.

Histology and histochemical staining of spinal cords: At time of sacrifice, spinal cords were removed and fixed in 10% (vol/vol) formalin in PBS buffer for 24 hours, then embedded in paraffin. Sections were cut at 5 μm on a microtome and stained by haematoxylin and eosin (H&E) to assess CNS inflammatory infiltrates and Luxol Fast Blue (LFB) to assess demyelinated areas following standard protocols.

Th1 and Th17 recall assays: At time of sacrifice, splenocytes were collected. After lysing the red blood cells, $0.4 \times 10^6$ of the splenocytes were incubated either without any peptide, 10 μg/ml of a non-relevant peptide ($IRBP_{1-20}$), or 10 μg/ml of the $MOG_{79-96}$ peptide in 100 μl of complete RPMI medium in each well of a 96 well plate. After 72 hours, IFN-γ and IL-17 levels in the culture supernatants were measured by respective ELISA following standard protocols.

In vitro Th1 and Th17 polarization assays: CD4+ T cells were isolated from gender and age-matched WT or CD6 KO mice by negative selection using magnetic beads (Easy-Sep™ Mouse CD4+ T Cell Isolation Kit, STEMCELL Technologies, Canada), then cultured under Th1 or Th17 polarization conditions following previously published protocols. Harrington, L. et al. Nature Immunology 6(11): 1123-1132 (2005). In brief, CD4+ T cells ($2 \times 10^4$ cells per well) were activated with plate-bound 5 μg/mL anti-CD28 (BioLegend), then cultured at 37° C. for 5 days. For Th1 polarization, activated cells were cultured in the presence of 20 ng/mL recombinant mouse IL-2, 25 ng/mL recombinant mouse IL-12 (PeproTech), and 10 μg/mL neutralizing anti-IL-4 antibody (BioLegend). For Th17 differentiation, activated T cells were cultured in the presence of 20 ng/mL recombinant mouse IL-6, 5 ng/mL recombinant moue TGF-β (PeproTech), and 10 μg/mL neutralizing anti-IL-4 and anti-IFN-γ antibodies (BioLegend). On days 1, 2, and 3, cells were stained with 5 μL of annexin V per sample followed by flow cytometric analysis according to a manufacturer-provided protocol (Annexin V Apoptosis Detection Kit, BD Biosciences). For the BrdU incorporation assay, cells were cultured in the presence (10 μM), and at different time points, the proliferation of the cells was assessed by measuring BrdU incorporation using a BrdU ELISA kit (Roche). Finally, differentiated Th1 and Th17 cells (day 5) were quantitated by intracellular staining of IFN-γ and IL-17. Harrington, L. et al. Nature Immunology 6(11): 1123-1132 (2005).

T cell activation marker regulation analysis: Purified WT or CD6 KO CD4+ T cells were activated by 1 μg/ml of anti-mouse-CD3 and anti-mouse-CD28 (Biolegend, San Diego, Calif.); 5 hours later, expression levels of activation markers CD25 and CD69 on the activated CD4+ T cells were measured by flow cytometry after staining with 2 μg/ml of both PE-anti-mouse CD69 and APC-anti-mouse CD25 mAbs (BioLegend, San Diego, Calif.).

Mouse primary BMEC isolation: Mouse BMEC were isolated following a previously published protocol. Ruck, T. et al. J Vis Exp (93): e52204 (2014). In brief, mouse brains were isolated, and the brainstems, cerebella, thalami, and meninges were removed under a dissecting microscope. The remaining tissue was minced and digested by 5 mg/mL collagenase CLS2 (Worthington Biochemical) in DMEM for 1 hour at 37° C., then washed with 20% (vol/vol) BSA-DMEM and centrifuged at 1,000×g for 20 minutes at 4° C. The pellet was resuspended in 1 mg/mL collagenase/dispase (Worthington Biochemical) and incubated for another 1 hour at 37° C. After the final washing, the resultant cells were cultured in endothelial cell medium (PeproTech). The isolated BMEC purity was determined by flow cytometric analysis after staining the cells with an anti-CD34 mAb (BioLegend).

Transwell T cell migration assay: Isolated WT BMEC were cultured onto the upper chambers of 3-μm pore size culture inserts (Falcon) in a 24-well transwell plate. After the cells formed a monolayer, $0.6 \times 10^6$ nylon wool-enriched splenic T cells [activated by 1 μg/mL of both anti-mouse CD3 and anti-mouse CD28 mAbs (BioLegend)] from matched WT and CD6 KO mice were added into the inserts with 20 ng/mL of mouse CCL2 [chemokine (C-C motif) ligand 2] (PeproTech) in the lower chambers (to facilitate T-cell migration), and cultured at 37° C. After 18 hours, the number of T cells remaining on top of the BMEC monolayer in the culture inserts and the number of migrated cells in the bottom chamber were counted by using a hemacytometer after Trypan blue staining and by flow cytometry. The percentages of cells remaining in the upper culture inserts and those that migrated into the lower chamber were calculated by using the following formula: %=cells in the upper inserts (or cells in the lower chambers)/(cells in the upper inserts+cells in the lower chambers)×100%.

Development of the CD6 humanized mice: CD6 humanized mice were developed by first generating a human CD6 (hCD6) transgenic (Tg) mouse in which hCD6 cDNA expression is driven by a human CD2 promoter (Zhumabekov et al., Journal of immunological methods 185: 133-140 (1995)) following conventional protocols at the transgenic core facility of Case Western Reserve University. An hCD6 high-expressing Tg mouse was identified by flow cytometry and bred with mCD6 KO mice to generate CD6 humanized mice (DBA-1 background). The CD6 humanized mice were typed by flow cytometry using respective anti-mCD6 and anti-hCD6 mAbs to ensure the presence of hCD6, but the absence of mCD6 on T cells (FIG. 7A, B).

EAE induction and treatment studies: EAE was induced in the CD6 humanized mice by active immunization with $MOG_{79-96}$ peptide as described above. Seven days after immunization, when mice developed mild clinical signs of EAE, they were randomly separated into two groups. One group was injected i.p. with 0.4 mg of a mouse anti-human CD6 IgG (UMCD6) (Singer, N. et al., Immunology 88(4): 537-543 (1996)) (0.4 mg per mouse) in the form of diluted ascites, and the other group received the same amount of purified mouse IgG (Jackson ImmunoResearch) as controls. Mice were then monitored and clinical scores recorded for another week. At the end of experiments, mice were euthanized, and peripheral blood lymphocytes were analyzed for percentages of CD4+, CD8+, or CD6+ T cells, splenocytes were used to carry out antigen-specific Th1 and Th17 recall assays, and spinal cords were analyzed by the same histological and histochemical assays as described above.

Statistical analysis: All experiments were repeated at least twice. To determine whether groups were statistically different, the clinical scores were analyzed by the ANOVA test while other results were compared using the Student t test. A $p$ value<0.05 was considered significant.

Results and Discussion

To study the role of CD6 in MS, experimental autoimmune encephalomyelitis (EAE) was induced in wild-type (WT) and CD6-knockout (KO) mice (FIG. 1) (both on DBA/1 background) by subcutaneous immunization of $MOG_{79-96}$ peptide. Abdul-Majid et al., J. Neuroimmunol, 111: 23-33 (2000). These experiments demonstrated that CD6 KO mice were protected compared to WT mice that developed severe EAE following immunization (FIG. 2A). Consistent with markedly reduced EAE severity, CD6 KO mice had reduced T cell infiltration and diminished demyelination in spinal cords (FIG. 2D, 2E). Recall assays showed decreased $MOG_{79-96}$-specific Th1 and Th17 responses in CD6 KO mice compared with those from WT mice (FIG. 2B, 2C). These results demonstrate that CD6 is required for the development of EAE, potentially by regulating pathogenic T cell responses and/or T cell infiltration into the CNS.

To elucidate the mechanism by which lack of CD6 reduces pathogenic Th1/Th17 responses and ameliorates disease severity in EAE, CD4+ T cells were isolated from naïve WT and CD6 KO mice, then cultured under Th1 or Th17 polarization conditions, followed by flow cytometric analysis of intracellular IFNγ (Th1) or IL-17 (Th17). In these experiments CD6 KO CD4+ T cells had impaired Th1 and Th17 development compared to WT CD4+ T cells (FIG. 3).

Previous studies using anti-CD6 mAbs to study the role of CD6 in T cell activation generated conflicting results. Some of the data suggest that CD6 provides co-stimulatory signals to enhance T cell activation and some suggest that CD6 inhibits T cell activation. Bott, C. et al., Int Immunol 5(7): 783-792 (1993); Singer, N. et al., Immunology 88(4): 537-543 (1996). To clarify the role of CD6 in T cell activation, WT and CD6 KO T cells were activated using anti-CD3 and anti-CD28 mAbs for 5 hours, then measured upregulation of T cell activation markers CD25 and CD69. The results demonstrate that, compared to WT T cells, CD6 KO T cells showed augmented upregulation of both CD25 (FIG. 4A) and CD69 (FIG. 4B), suggesting that CD6 is a negative regulator of T cell activation.

The discovery that CD6 is a negative regulator of T cell activation appears to conflict with results from the above EAE studies which showed decreased Th1/Th17 responses in CD6 KO mice. To address this paradox, WT and CD6 KO CD4+ T cells were again activated under Th1 or Th17 polarization conditions and T cell apoptosis was compared at 5, 24, 48 and 72 hours by Annexin V staining. After activation under both Th1 and Th17 polarization conditions, CD6 KO T cells underwent significantly more apoptosis (Annexin $V^+$) than WT T cells (FIG. 5A, 5B).

In addition to activation and survival, proliferation of activated T cells also governs the outcome of a T cell response. Proliferation of activated WT and CD6 KO T cells was therefore measured under Th1 or Th17 polarization conditions at 5, 24, 48 and 72 hours after activation, by a BrdU incorporation assay. In the absence of CD6, activated T cells under both Th1 and Th17 polarization conditions had significantly reduced proliferation (FIG. 5C, 5D).

In EAE, activated pathogenic Th1 and/or Th17 cells need to migrate through the BBB into the CNS to initiate local inflammation, and BMECs are an important component of the BBB. To determine whether CD6 has an effect on activated T cell migration through the BBB, BMECs were first isolated from naïve WT mice following an established protocol (Ruck, T. et al., J Vis Exp (93): e52204 (2014)) (FIG. 6A, B), then these cells were grown into monolayers on culture inserts in transwell culture plates. Carboxyfluorescein succinimidyl ester (CFSE)-labeled WT or CD6 KO T cells activated with anti-CD3/anti-CD28 mAbs were added onto the top of the monolayer of BMEC; CCL2 [Chemokine (C-C motif) ligand 2] was added to the bottom of the transwells to induce T cell migration. After 18 hours of incubation, WT T cells migrated better than the CD6 KO T cells through the BMEC monolayer (FIG. 6C), suggesting that CD6 on T cells is required for activated T cells to efficiently migrate through the BBB to initiate inflammation in EAE.

To test the potentials of existing mouse anti-human CD6 mAbs for future humanization and clinical development to treat MS patients, a human CD6 transgenic mouse (hCD6 Tg) was generated in which human CD6 cDNA expression is driven by a human CD2 promoter/locus control region to reproduce the relative restriction of human CD6 to T-cells. de Boer et al., Eur J Immunol 33: 314-325 (2013). After verifying the expression of human CD6 protein on lymphocytes in the resultant Tg mice, the human CD6 Tg mice was backcrossed onto the DBA-1 background, then the human CD6 Tg mice was bred with the mouse CD6 KO mice, and CD6 humanized mice that do not express mouse CD6 (FIG. 7A) but instead express human CD6 in vivo (FIG. 7B) were generated.

To demonstrate that human CD6 can replace mouse CD6 function in vivo and that these newly developed humanized mice can be used to test CD6-targeted reagents that have potential in treating human diseases, and to evaluate the mouse anti-human CD6 mAb for its potential in treating MS, EAE was induced in the humanized CD6 mice (DBA-1 background). Humanized mice were immunized with $MOG_{79-96}$ peptide in CFA together with pertussis toxin, per protocol described above, then the development of EAE was assessed by monitoring clinical scores daily. Once mice showed mild signs of EAE clinically, half of the mice were randomly treated with a mouse anti-human CD6 IgG (UMCD6) (~ 0.4 mg/mouse) and the other half with the same amount of mouse IgG by i.p. injection, then the mice were continued to be monitored daily. Immunological and histopathological assays were also carried out as described. These experiments showed that, like WT DBA-1 mice, humanized CD6 mice developed severe EAE (FIG. 7C), indicating that transgenic expression of human CD6 can replace the function of mouse CD6 in mice, and supporting the hypothesis that using CD6 humanized mice can predict the effects of CD6-related reagents in human MS. Compared with severe EAE that developed in humanized CD6 mice treated with control mouse IgG, EAE progression in the treated mice was halted, and these mice showed little clinical evidence of EAE 7 days after treatment (FIG. 7C). Recall assays showed significantly reduced MOG-specific Th1 (FIG. 7D) and Th17 responses (FIG. 7E) in the active treatment group compared to control. Further, histopathological assays showed markedly decreased spinal cord inflammation (FIG. 7F) and reduced demyelination (FIG. 7G) in the treated mice.

Because CD6 is present on all T cells, one possible mechanism by which the anti-CD6 mAb ameliorates EAE severity could be depletion of T cells. To test this, CD4+ and CD8+ T cell percentages in the UMCD6-treated and control IgG-treated mice was assessed by staining the peripheral leukocytes with anti-CD4, anti-CD8 and a polyclonal anti-hCD6 IgG (R&D). These experiments found that CD4+, CD8+ and CD6+ T cell populations did not significantly change between the treated and control groups (FIG. 8), suggesting that UMCD6 mAb attenuated EAE disease severity in the CD6 humanized mice neither by T cell depletion nor by modulating CD6 on T cells.

These data are the first to provide in vivo evidence demonstrating that lack of CD6 protects mice from CNS in EAE in association with reduced pathogenic Th1/Th17 responses and decreased T-cell infiltration into the CNS. Additionally, a mouse anti-human CD6 mAb (UMCD6) was shown to be highly effective in treating EAE without depleting T cells.

CD6 was shown to be a negative regulator of T cell activation and, at the same time, a positive regulator of T cell proliferation and survival. The cumulative effects of CD6 on T cell activation, proliferation, and apoptosis together result in CD6 KO T cells differentiating into far fewer IFN-γ-producing Th1 or IL-17-producing Th17 cells compared with WT T cells. The observation that recall responses to MOG peptide ex vivo showed reduced IFNγ and IL-17 secretion in CD6 KO splenocytes compared to WT splenocytes support that absence of CD6 reduces production of pro-inflammatory cytokines during memory responses.

Even though certain CD6 polymorphisms have been associated with susceptibility to MS (International Multiple Sclerosis Genetics C., PLoS One 6(4): e18813 (2011); Heap, G. et al., Hum Mol Genet 19(1): 122-134 (2010)), the pathogenic role of CD6 in MS is still unclear. Surprisingly, in in vitro assays, activated T cells from patients carrying a CD6 risk allele have impaired proliferation comparing to T cells from donors carrying the non-risk allele. Kofler, D. et al., Journal of Immunology 187(6): 3286-3291 (2010). By studying WT and CD6 KO mice in EAE, the inventor found that the absence of CD6 protected mice from CNS injury in EAE indicating that CD6 is required for the development of EAE, and potentially, MS. The inventor's in vitro T cell activation, proliferation and survival studies provided insights into the mechanisms underlying the observed reduced MOG-specific Th1 and Th17 responses in the CD6 KO mice in EAE. It appears that after EAE induction in the CD6 KO mice, although MOG-specific T cells were initially activated more robustly, their differentiation into IFNγ-secreting Th1 and IL-17-secreting Th17 cells was less efficient and they died faster than did T cells in WT mice, leading to reduced MOG-specific Th1/Th17 responses, and, eventually, attenuated EAE.

The inventor's H&E studies also showed that there was significantly reduced cell infiltration in the CNS of CD6 KO mice after EAE induction. To distinguish whether CD6 expression also affected the ability of T cells to infiltrate to the CNS, the inventor performed in vitro T cell migration assays comparing the capacity of CD6 KO T cells and WT T cells to migrate through a monolayer of BMEC. The data showed that CD6 is also required for T cells to infiltrate with optimal efficiency through the BMEC monolayer. This implies that CD6 is important for migration of T cells through the BBB into the CNS, which is known to be a critical step in development and/or progression of both EAE and MS.

Speculation that CD6 is a good target for treating autoimmune diseases including MS has existed for decades (Pinto, M & Carmo, A., BioDrug 27(3): 191-202 (2013)) but, the first and only clinical study conducted more than 30 years ago using a T cell-depleting mouse anti-human CD6 IgM for treating MS patients was inconclusive. Hafler, D. et al., Neurology 36(6): 777-784 (1986). Data that CD6 deficiency leads to reduced Th1 and Th17 polarization in vitro and that CD6 KO mice are protected from CNS injury in EAE in vivo strongly argue that CD6-targeted reagents, useful for treating EAE, merit re-evaluation as a potential approach to MS. Since all the available anti-human CD6 mAbs were developed in mice, and previous studies suggest that CD6 binds to its ligand without species restrictions (Bowen, M., et al., Eur J Immunol 27(6): 1469-1478 (1997)), the inventor developed a CD6 humanized mouse in which human CD6 replaces mouse CD6 on T cells. These animals can be used to screen mouse anti-human CD6 mAbs for future development without confounding immunogenicity issues in mice. The inventor's results that CD6 KO mice are resistant to EAE induction and that the restoration of human CD6 in the CD6 KO mice (CD6 humanized mice) is associated with severe EAE after immunization provide clear evidence that human and mouse CD6 function interchangeably in mice as previously predicted. Bowen, M. et al., Eur J Immunol 27(6): 1469-1478 (1997). Thus, these CD6 humanized mice are invaluable to identify effective human CD6-targeted reagents, including human CD6-targeted mAbs in the EAE model of human MS and potentially in other models of human autoimmune diseases.

While there is no current CD6-related clinical trial in the US and Europe, Itolizumab, an anti-human CD6 mAb developed in Cuba has been effective in reducing pathogenic T cell responses in psoriasis patients and was recently approved for treating psoriasis in India. Menon, R & David, B, Clin Cosmet Investig Dermatol 8: 215-222 (2015). Itolizumab combined with methotrexate has also been reported to reduce T cell numbers and pro-inflammatory cytokine levels in patients with rheumatoid arthritis, although the clinical outcomes still need to be defined. Aira, L, et al., mAbs 8(1): 187-195 (2016). Surprisingly, Itolizumab binds to domain 1 of CD6 (Alonso, R, et al., Hybridoma (Larchmt) 27(4): 291-301 (2008)) and it does not block the interaction between CD6 and its currently known ligand, CD166, which binds to domain 3 of CD6. Chappell, P, et al., Structure 23(8): 1426-1436 (2015). Interestingly, the anti-human CD6 mAb (UMCD6) that the inventor used to treat EAE in CD6 humanized mice also binds to domain 1 of CD6 and does not block CD6-CD166 interaction. Singer, N. et al., Immunol Lett 58(1): 9-14 (1997). Thus both in vitro and in vivo studies employing anti-CD6 mAbs suggest that the CD6-CD166 interaction might not be critical for CD6 function in disease, at least not in psoriasis or MS. Instead, a new ligand that interacts with domain 1 of CD6 could be a more important CD6 partner than CD166.

A recent report has used CD6$^{-/-}$ mice to assess the role of CD6 in T cell development and activation. Orta-Mascaró, M., et al., J Exp Med 213(8): 1387-1397 (2016). This study found subtle aberrations in single-positive thymocyte and mature T cell subsets in CD6$^{-/-}$ TCR transgenic mice. The severity of collagen-induced arthritis was enhanced in CD6$^{-/-}$ mice, in apparent contrast to the current results in the EAE model. It is worth noting that the CIA studies were conducted in C57BL/6 mice, a strain in which the incidence and severity of CIA is substantially less compared to the DBA-1 strain (the strain that the inventor used for the EAE studies). Additional studies will be required to unravel the reasons that underlie the apparent differences between distinct autoimmune models and genetically distinct mouse strains in the role of CD6 in the development of autoimmune disease, and whether such differences are paralleled by heterogeneity in the roles of CD6 in various human autoimmune conditions. Nevertheless, the results in CIA and the current data both highlight an emerging appreciation of the potentially pivotal role of CD6 in control of T-cell driven autoimmunity.

In summary, using WT and CD6 KO mice, the inventor demonstrated that CD6 is required for the development of EAE. CD6 is a negative regulator of T cell activation, but a positive regulator of T cell proliferation and survival. Therefore, lack of CD6 leads to reduced T cell responses in EAE. In addition, CD6 on T cells is also required for T cell infiltration through the BBB into the CNS. By developing a CD6 humanized mice, the inventor showed that human CD6 functions in mice, and identified UMCD6, a mouse anti-human CD6 mAb, as a potent inhibitor of EAE. These results encourage exploration of the potential of a humanized variant of an anti-CD6 antibody such as UMCD6 to become a new therapeutic for treating MS and possibly other diseases.

Example 2: Antibody Humanization

This example describes work directed to humanize an anti-CD6 mouse monoclonal antibody without sacrificing the binding affinity. The humanization was carried out using two approaches: one is phage display library-based 'framework assembly' method; the other is structure-based CDR (complementarily determining region) grafting with framework back-mutations.

The following experiments were carried out to prepare a humanized anti-CD5 mouse monoclonal antibody. 1. Generation of phage display library; 2. Selection of humanized antibodies from phage display library and FASEBA screening; 3. Antibody humanization by CDR grafting (structure-based method) with framework back-mutations; and 4. Production and characterization of humanized antibodies.

Methods

Generation of humanization phage display library: The combinatorial humanization phage display library was designed according to GenScript's proprietary technology 'Antibody humanization by framework assembly'; U.S. Pat. No. 9,090,994, the disclosure of which is incorporated herein by reference. Briefly, frameworks of human antibodies with high sequence identities to the mouse antibody (GenScript sequencing No. 353920) were selected, randomly combined and assembled. Then the CDRs of mouse antibody were grafted to the assembled combinatorial human frameworks. The construction of library was carried out following GenScript's standard operating procedures (SOP).

Isolation of humanized antibody binders from phage display library: The humanized Fab phage display library was panned against rhCD6-Fc. Individual output phage clones were amplified in 96-deep-well plates and the amplified phage clones were assayed by ELISA against rhCD6-Fc. Bound phage clones were detected using a HRP/Anti-M13 monoclonal antibody. Phage clones with ELISA signal-to-noise ratios larger than 2.1 were considered to be able to bind rhCD6-Fc. The panning ended after two rounds when a good percentage of phage clones were found to bind rhCD6-Fc. Panning and phage ELISA were carried out following GenScript's SOP.

Humanization by CDR grafting: Selection of acceptor frameworks: The variable domain sequences of the parent mouse monoclonal antibody were searched against the database of germline and rearranged Ig variable region sequences using NCBI Ig-Blast. The variable domains which have structures available in Protein Data Bank (PDB) and show the highest sequence identities to those of parent antibody variable region sequences were used to generate a homology model of parent antibody. Human sequences with highest identities to parent antibody variable region sequences were identified. The CDRs of human acceptors were replaced by those of parent antibody.

FASEBA Screening, Affinity Ranking and Cell Binding Validation by FACS

FASEBA screening, affinity ranking: DNAs encoding Fab fragments of the output phage were amplified and inserted into pFASEBA vector for screening of the lead antibodies. Individual FASEBA library clones were inoculated and induced for expression in 96-deep-well plates. ELISA screening was performed to isolate Fabs which recognize rhCD6-Fc specifically, and the expression medium were selected for affinity ranking by BIAcore T200.

BSA was immobilized onto the sensor chip using amine coupling method. The selected Fab-SASA clones secreted to the culture medium were injected and captured by BSA via SASA (capture phase). After equilibration, antigen rhCD6-Fc was injected for 240 seconds (association phase) followed by the injection of running buffer for 720 seconds (dissociation phase). The surface was regenerated before the injection of another three Fab-SASA clones. Repeat the process until all antibodies are analyzed. Responses of reference flow cell were subtracted from those of Fab-SASA flow cells during each cycle. The binding curves of Fab-SASA clones were aligned at the start of association and normalized at 20 seconds after the stop of antigen injection using the BIAcore T200 evaluation software in order to display a more visualized comparison of antibodies. The off-rates of Fab-SASA clones were obtained from fitting the experimental data locally to 1:1 binding model. The antibodies were ranked by their dissociation rate constants. Single cycle kinetics measurement was performed to verify the affinity ranking result. The selected Fab-SASA clones secreted to the culture medium were injected and captured by BSA via SASA (capture phase). After equilibration, a series of concentrations of antigen rhCD6-Fc (1, 3, 9, 27 and 81 nM) were injected for 500 seconds (association phase) followed by the injection of running buffer for 3000 seconds (dissociation phase). The surface was regenerated before another injection of Fab-SASA clones. Responses of reference flow cell and buffer-only injection were double-subtracted from those of Fab-SASA flow cells during each antigen injection cycle. The binding data were fitted to 1:1 binding model using the BIAcore T200 evaluation software.

BSA was immobilized onto the sensor chip using amine coupling method. The selected Fab-SASA clones secreted to the culture medium were injected and captured by BSA via SASA (capture phase). After equilibration, antigen rhCD6-Fc was injected for 240 seconds (association phase) followed by the injection of running buffer for 720 seconds (dissociation phase). The surface was regenerated before the injection of another three Fab-SASA clones. The process was repeated until all antibodies were analyzed. Responses of reference flow cell were subtracted from those of Fab-SASA flow cells during each cycle. The binding curves of Fab-SASA clones were aligned at the start of association and normalized at 20 seconds after the stop of antigen injection using the BIAcore T200 evaluation software in order to display a more visualized comparison of antibodies. The off-rates of Fab-SASA clones were obtained from fitting the experimental data locally to 1:1 binding model. The antibodies were ranked by their dissociation rate constants Single cycle kinetics measurement was performed to verify the affinity ranking result. The selected Fab-SASA clones secreted to the culture medium were injected and captured by BSA via SASA (capture phase). After equilibration, a series of concentrations of antigen rhCD6-Fc (1, 3, 9, 27 and 81 nM) were injected for 500 seconds (association phase) followed by the injection of running buffer for 3000 seconds (dissociation phase). The surface was regenerated before another injection of Fab-SASA clones. Responses of reference flow cell and buffer-only injection were double-subtracted from those of Fab-SASA flow cells during each antigen injection cycle. The binding data were fitted to 1:1 binding model using the BIAcore T200 evaluation software.

Cell binding validation by FACS: For cell binding validation of Fabon Jurkat cells, flow cytometry analysis was performed using the culture supernatant. Jurkat cells were grown to 70-80% confluence and harvested by centrifuge. About $4 \times 10^5$ cells per well were washed with PBS twice. 200 µl individual culture supernatant of protein positive clone was added to the cells and incubated at room temperature for 1 h. After washing with PBS, antibody was added to the cells for the detection of bound Fab. After 30 minutes incubation, the cells were washed twice with PBS and resuspended in PBS. Cells were analyzed for Fab binding by FACS Calibur (BD Bioscience, San Jose, Calif.) and Flowjo software.

Expression and Purification of Selected Antibodies

Expression of antibodies: For each transfection, 125 µg each of light chain and heavy chain expression plasmids were pre-mixed with 750 µl Polyethylenimine (PEI) stock solution (1 mg/ml) and 10 ml pre-warmed Freestyle 293 medium, then the mixture was incubated for 10 minutes at room temperature to allow complexes to form. The mixture was added into 240 ml of suspended HEK293-6E cell culture in Freestyle 293 medium at a cell density of approximately $2.0 \times 10^6$ cells per ml. The mixture was transferred into a 1-L shaker flask, and incubated at 37° C. and 5% $CO_2$ on an orbital shaker rotating with constant shaking at 110 rpm. Pre-warmed TN1 was added into the cell culture with a final concentration of 0.5% (w/v) at 24 h post-transfection. Harvest the conditioned medium on 5~6 days post-transfection by centrifugation at 1500×g for 10 minutes to remove cells. The supernatants were used for the subsequent antibody purification.

Characterization of Humanized Antibodies

Affinity analysis of antigen-antibody interaction: The affinities of antibodies binding to the antigen rhCD6-Fc were determined using a BIAcore T200 SPR system (GE Healthcare) at 25° C. in HBS-EP buffer (10 mM HEPES, 150 mM NaCl, 3 mM EDTA, 0.005% (v/v) Tween 20, pH 7.4). For the measurement of three humanized antibody affinities for rhCD6-Fc, rhCD6-Fc (diluted at 2 µg/ml in 10 mM sodium acetate, pH 5.0) was immobilized on Series S CM5 chips by amine coupling at a density of ~100 RU. IgG antibodies were injected through flow cells at a flow rate of 30 µl/min with the concentration ranging from 0.11~27 nM (three-fold serial dilution). Association time was 700 s followed by 3600 s dissociation. At the end of each cycle, sensor surface was regenerated with 10 mM Glycine-HCl, pH 2.0 (100 µl/min, 12 s for 3 times). Responses of reference flow cell and buffer-only injection were double-subtracted from rhCD6-Fcflow cell during each antigen injection cycle. The data of dissociation (kd) and association (ka) rate constants were obtained by fitting binding data to 1:1 binding model using Biacore T200 evaluation software. The apparent equilibrium dissociation constants (KD) were calculated from the ratio of kd over ka.

Binding $IC_{50}$ measurement of humanized IgGs by FACS: Flow cytometric analysis was performed using the purified antibodies. Jurkat cells were grown to 70-80% confluence and harvested by centrifuge. About $4 \times 10^5$ cells per well were washed with PBS twice. 200 µl of the culture supernatant was added to the cells and incubated at room temperature for 1 hour. After washing with PBS, antibody was added to the cells for the detection of bound humanized IgG. After 30 minutes incubation, the cells were washed twice with PBS and resuspended in PBS. Cells were analyzed for IgG binding by using FACS Calibur (BD Bioscience, San Jose, Calif.) and Flowjo software. The $IC_{50}$ was analyzed by GraphPad Prism.

Thermostability measurement by Circular Dichroism (CD): The far-UV CD spectra of IgG at increasing temperatures were recorded using Jasco J-815 CD spectrometer (Jasco Inc.). The temperature-induced IgG denaturation was recorded by the changes in ellipticity at 202 and 208 nm. The temperature at transition midpoint (Tm) was obtained by fitting a two-state denaturation model in which only native and denatured states are present in the equilibrium to the experimental data. Data analysis was carried out using Prism 4 (GraphPad Software, Inc.).

Results

Isolation of humanized antibody binders from phage display library. Two rounds of panning were performed to enrich the humanized binders. The positive rate (the number of antigen-specific humanized clone over the number of randomly picked clones) of the first round was around 2%. After the second round of panning, the binders were enriched and the positive rate reached around 40%. The Fab DNAs of the second round output phage were inserted to pFASEBA vector for FASEBA screening.

TABLE 1

Details of panning and phage ELISA experiments.

| Round | Input (pfu) | Output (pfu) | Positive rate of phage ELISA |
|---|---|---|---|
| 1st | $2.0 \times 10^{10}$ | $3.0 \times 10^4$ | 1.7% |
| 2nd | $2.0 \times 10^{10}$ | $1.5 \times 10^3$ | 39.1% |

Structure-based humanization by complementarity-determining region (CDR) grafting with framework back-mutations. Homology modeling of the parent antibody variable fragments was carried out using Discovery Studio v5.0 (Accelrys). Parent antibody variable region sequences were BLAST searched against the Protein Database (PDB) antibody database for identifying the best templates for antibody variable region fragments and especially for building the domain interface. Homology models were built using customized Build Homology Models protocol. Disulfide bridges were specified and linked. Loops were optimized using DOPE method. Based on the homology models of parent antibody variable regions, all framework residues in the proximity, i.e. within 5 Å, of all CDR residues and in the hydrophobic core or $V_H/V_L$ interface of the antibody were identified. One CDR grafting and seven back-mutation constructs were designed for this project (CDRs are shown as underlined amino acids, back-mutation residues are shown in bold, Table 2). Table 2 discloses SEQ ID NOS 11, 2, 12, 13, 1, 2, 3, 2, 14, 2, 15, 2, 16, 2, 17, and 2, respectively, in order of appearance.

TABLE 2

Sequences of humanized antibody variants.

| Name | Sequence |
|---|---|
| 1 | VH QVQLQESGPGLVKPSETLSLTCTVSGGSIS<u>RYSVHW</u>IRQPPG KGLEWIG<u>LIWGGGFTDYNSALKS</u>RVTISVDTSKNQFSLKLSS VTAADTAVYYCAR<u>EGVAY</u>WGQGTLVTVSS VL DVVMTQSPLSLPVTLGQPASISC<u>KSSQSLLNSDGRTYLN</u>WFQ QRPGQSPRRLIY<u>LVSKLDS</u>GVPDRFSGSGGTDFTLKISRVEA EDVGVYYC<u>WQGTHFPFT</u>FGPGTKVDIK |

TABLE 2-continued

Sequences of humanized antibody variants.

| Name | Sequence |
|---|---|
| 3 | VH QVQLQESGPGLVKPSETLSLTCTVSGGSISRYSVHWIRQPPG<br>KGLEWIGLIWGGGFTDYNSALKSRVSITVDTSKNQFSLKLSS<br>VTAADTAVYYCAREGVAYWGQGTLVTVSS<br>VL DVVMTQSPLSLPVTLGQPASISCKSSQSLLNSDGRTYLNWFQ<br>QRPGQSPKRLIYLVSKLDSGVPDRFSGSGGTDFTLKISRVEA<br>EDVGVYYCWQGTHFPFTFGPGTKVDIK |
| 2 | VH QVQLQESGPGLVKPSETLSLTCTVSGFSLSRYSVHWVRQPPG<br>KGLEWLGLIWGGGFTDYNSALKSRLTISKDNSKNQVSLKLSS<br>VTAADTAVYYCAREGVAYWGQGTLVTVSS<br>VL DVVMTQSPLSLPVTLGQPASISCKSSQSLLNSDGRTYLNWFQ<br>QRPGQSPRRLIYLVSKLDSGVPDRFSGSGGTDFTLKISRVEA<br>EDVGVYYCWQGTHFPFTFGPGTKVDIK |
| 4 | VH QVQLQESGPGLVKPSETLSLTCTVSGFSISRYSVHWIRQPPG<br>KGLEWIGLIWGGGFTDYNSALKSRVTISKDNSKNQVSLKLSS<br>VTAADTAVYYCAREGVAYWGQGTLVTVSS<br>VL DVVMTQSPLSLPVTLGQPASISCKSSQSLLNSDGRTYLNWFQ<br>QRPGQSPRRLIYLVSKLDSGVPDRFSGSGGTDFTLKISRVEA<br>EDVGVYYCWQGTHFPFTFGPGTKVDIK |
| 5 | VH QVQLQESGPGLVKPSETLSLTCTVSGGSLSRYSVHWVRQPPG<br>KGLEWLGLIWGGGFTDYNSALKSRLTISVDTSKNQFSLKLSS<br>VTAADTAVYYCAREGVAYWGQGTLVTVSS<br>VL DVVMTQSPLSLPVTLGQPASISCKSSQSLLNSDGRTYLNWFQ<br>QRPGQSPRRLIYLVSKLDSGVPDRFSGSGGTDFTLKISRVEA<br>EDVGVYYCWQGTHFPFTFGPGTKVDIK |
| 6 | VH QVQLQESGPGLVKPSETLSLTCTVSGFSLSRYSVHWIRQPPG<br>KGLEWIGLIWGGGFTDYNSALKSRVTISKDNSKNQVSLKLSS<br>VTAADTAVYYCAREGVAYWGQGTLVTVSS<br>VL DVVMTQSPLSLPVTLGQPASISCKSSQSLLNSDGRTYLNWFQ<br>QRPGQSPRRLIYLVSKLDSGVPDRFSGSGGTDFTLKISRVEA<br>EDVGVYYCWQGTHFPFTFGPGTKVDIK |
| 7 | VH QVQLQESGPGLVKPSETLSLTCTVSGGSISRYSVHWVRQPPG<br>KGLEWLGLIWGGGFTDYNSALKSRLTISVDTSKNQFSLKLSS<br>VTAADTAVYYCAREGVAYWGQGTLVTVSS<br>VL DVVMTQSPLSLPVTLGQPASISCKSSQSLLNSDGRTYLNWFQ<br>QRPGQSPRRLIYLVSKLDSGVPDRFSGSGGTDFTLKISRVEA<br>EDVGVYYCWQGTHFPFTFGPGTKVDIK |
| 8 | VH QVQLQESGPGLVKPSETLSLTCTVSGGSLSRYSVHWVRQPPG<br>KGLEWIGLIWGGGFTDYNSALKSRLTISVDTSKNQVSLKLSS<br>VTAADTAVYYCAREGVAYWGQGTLVTVSS<br>VL DVVMTQSPLSLPVTLGQPASISCKSSQSLLNSDGRTYLNWFQ<br>QRPGQSPRRLIYLVSKLDSGVPDRFSGSGGTDFTLKISRVEA<br>EDVGVYYCWQGTHFPFTFGPGTKVDIK |

FASEBA Screening, Off-Rate Ranking and Cell Binding Validation by FACS

Figure 9:
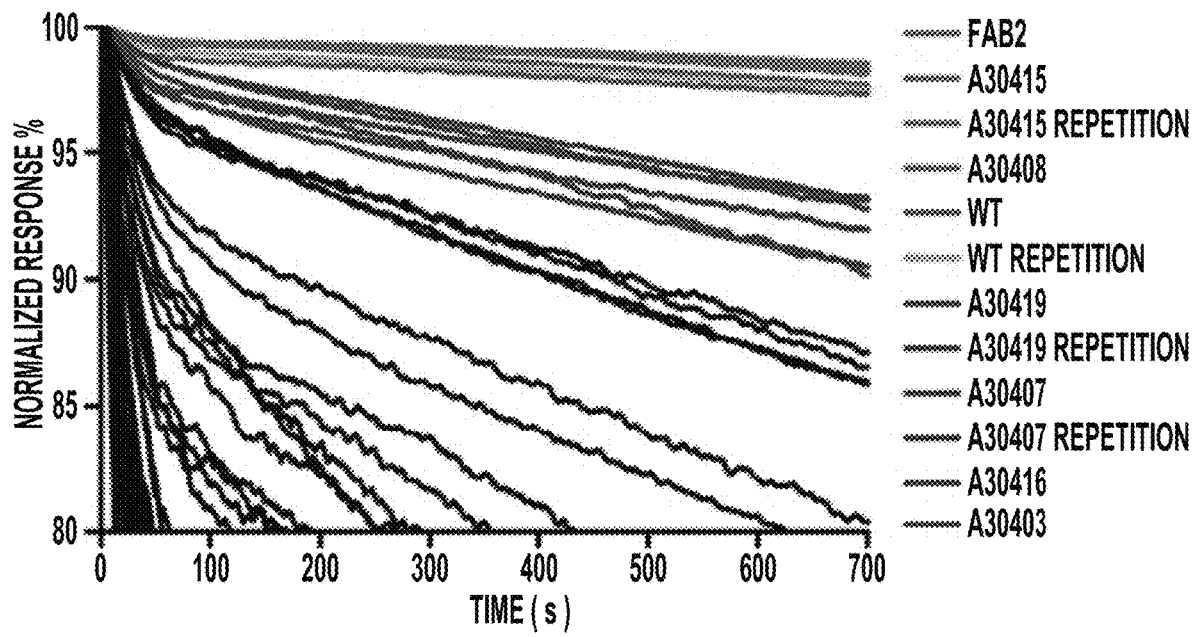
FIG. 9 provides a sensorgram showing the off-rate analysis of secreted Fab antibodies to rhCD6-Fc. The top 6 high affinity binders were selected for single cycle kinetics analysis.
Figure 10:
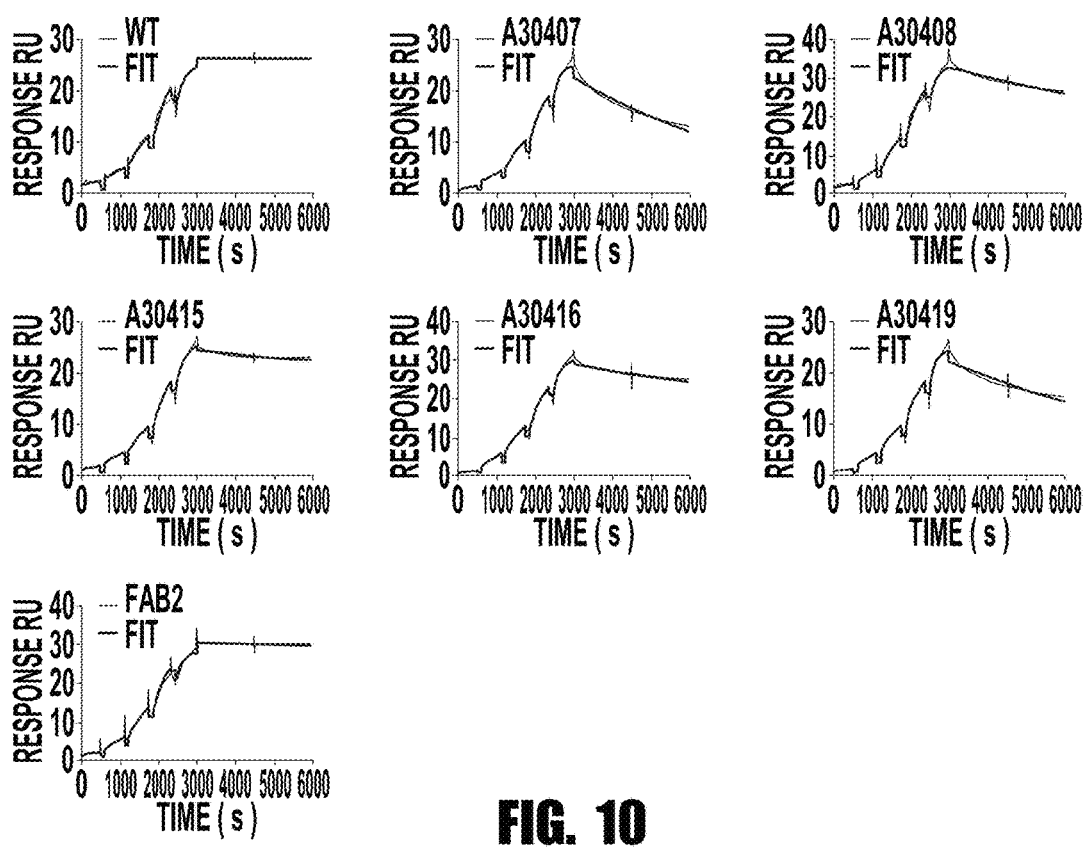
FIG. 10 provides a sensorgram of a single cycle kinetics analysis of secreted Fab antibodies to rhCD6-Fc. Only the affinity of Fab2 is comparable to WT Fab (parent chimeric antibody).

FASEBA screening, affinity ranking and FACS validation from phage display library. DNAs encoding Fab fragments of second round output phage were amplified and inserted into pFASEBA vector for screening of the lead antibodies by ELISA. 600 clones were selected through FASEBA ELISA screening. Forty five clones were sent for DNA sequencing and screened for binding test against rhCD6-Fc and subsequent off-rate analysis by the BIAcore T 200. Five clones from the library and Fab2 from CDR grafting were selected for single cycle kinetics analysis due to the low dissociation rate using the BIAcore T200 evaluation software (FIG. 9). And only Fab2 (refer to the sequence of back-mutation 2) with 8 point back mutations is comparable to WT Fab (parent chimeric antibody) according to single cycle kinetics analysis (FIG. 10).

Figure 11:
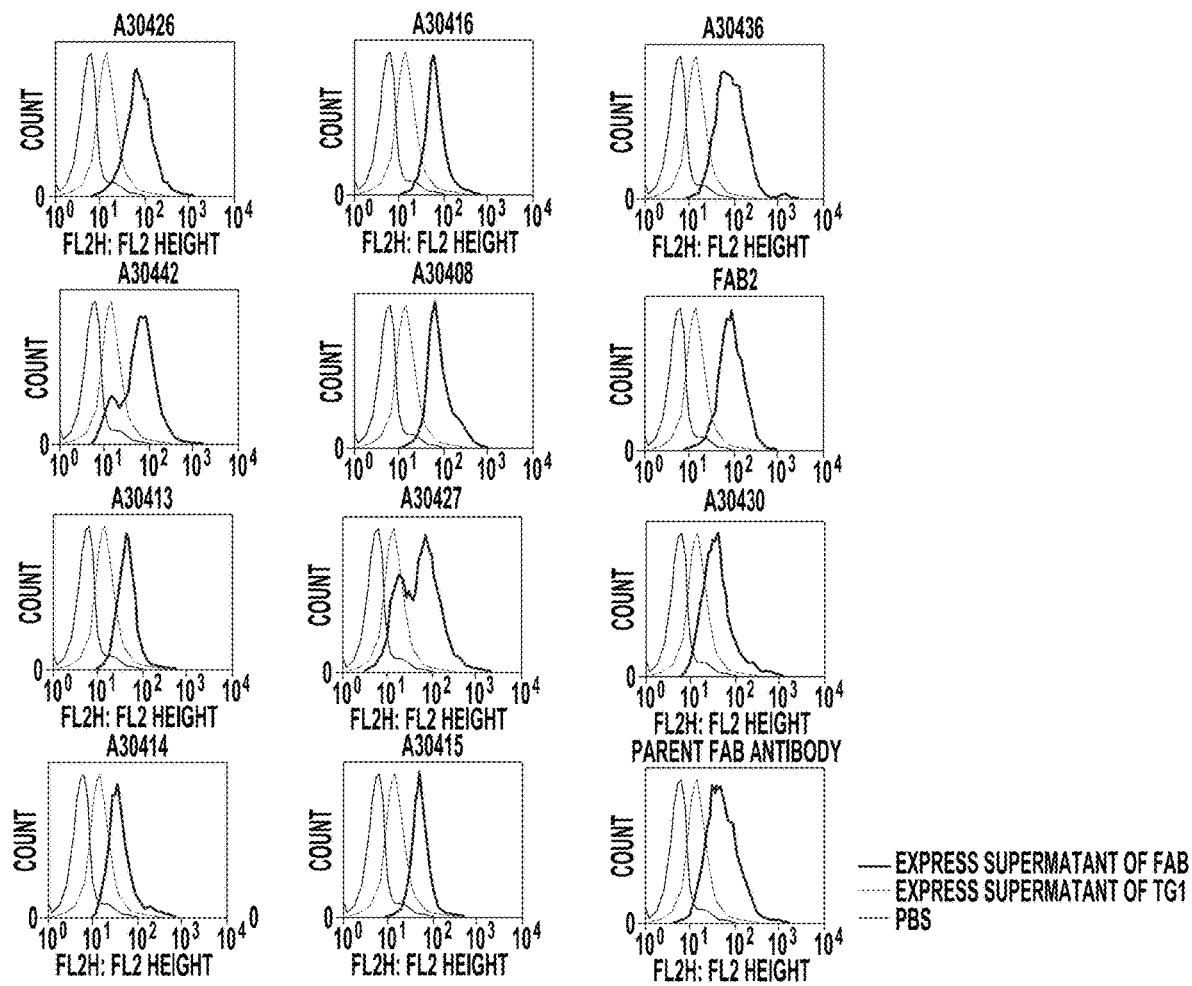
FIG. 11 provides graphs showing cell binding validation of 11 selected humanized clones by FACS using Jurkat cells.

According to the affinity ranking results, top 10 clones with slowest off-rate and Fab2 clone from CDR grafting were selected for cell binding validation by FACS. WT Fab (parent chimeric antibody) served as a positive control. FIG. 11 indicates the binding of 11 clones are comparable with that of WT Fab (parent chimeric antibody) (FIG. 11).

Five back-mutation clones were constructed based on sequence of Fab2 and homology modeling. Each of DNA sequence encoding the five Fab fragments was inserted into pFASEBA vector for screening of the lead antibodies. The five clones along with Fab2 were screened against rhCD6-Fc for binding test and subsequent off-rate analysis by the BIAcore T200. Three clones were selected for IgG production and characterization due to the low dissociation rate using the BIAcore T200 evaluation software (Table 3). The nucleotide and amino acid sequences for the selected clones (Fab2, Fab4, and Fab6) are shown in FIGS. 16, 17, and 18, respectively, while the sequences for the $V_L$ region are shown in FIG. 19.

TABLE 3

Kinetic data of selected Fab clones.

| Sample ID | $K_d(1/s)$ |
|---|---|
| WT Fab (parent chimeric antibody) | <5E−06 |
| WT Fab R (parent chimeric antibody) | <5E−06 |
| Fab4 | 1.9E−05 |
| Fab2 | 2.1E−05 |
| Fab6 | 3.1E−05 |
| Fab5 R | 5.3E−04 |
| Fab5 | 5.6E−04 |
| Fab7 | 8.9E−04 |
| Fab8 | No expression |

Figure 12:
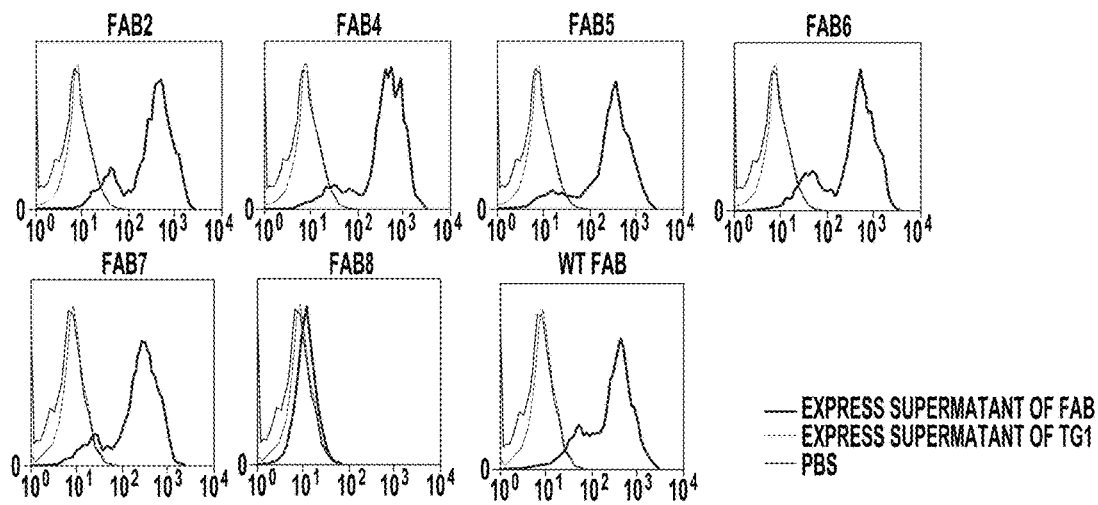
FIG. 12 provides graphs showing cell binding validation of 6 selected Fab clones by FACS using Jurkat cells.

FACS validation of back-mutation clones binding to Jurkat cells. Five back-mutation Fab clones were selected along with Fab2 for cell binding validation by FACS (FIG. 12). According to the FIG. 8, all the back-mutation clones have comparable binding on Jurkat cells except Fab8, which doesn't express well.

Expression and Purification

Figure 13:
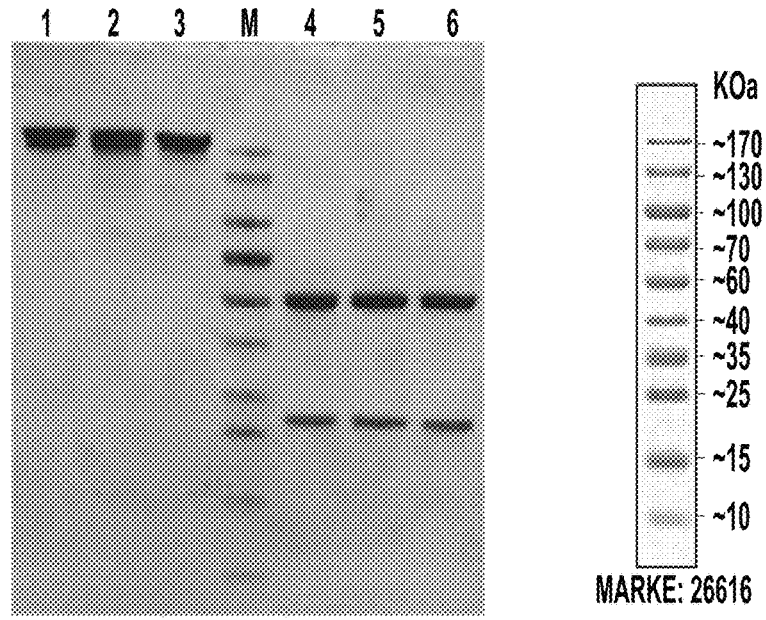
FIG. 13 provides SDS-PAGE analysis of three purified humanized antibodies. Lane 1, 2 μg purified Humanized IgG2 under non-reducing condition; Lane 2, 2 μg purified Humanized IgG4 under non-reducing condition; Lane 3, 2 μg purified Humanized IgG6 under non-reducing condition; Lane 4, 2 μg purified Humanized IgG2 under reducing condition; Lane 5, 2 μg purified Humanized IgG4 under reducing condition; Lane 6, 2 μg purified Humanized IgG6 under reducing condition; Lane M, page ruler pre-stained protein ladder (Thermo Scientific, Cat. No.: 26616)

The purified Humanized IgG2, Humanized IgG4 and Humanized IgG6 were analyzed by SDS-PAGE. The purified proteins have a molecular weight of ~170 kDa with purity of >90% under both reducing and non-reducing conditions (FIG. 13). About 2.0 mg of Humanized IgG2, 2.3 mg of Humanized IgG4 and 2.6 mg Humanized IgG6 were obtained from each 250 ml culture.

Characterization

Figure 14:
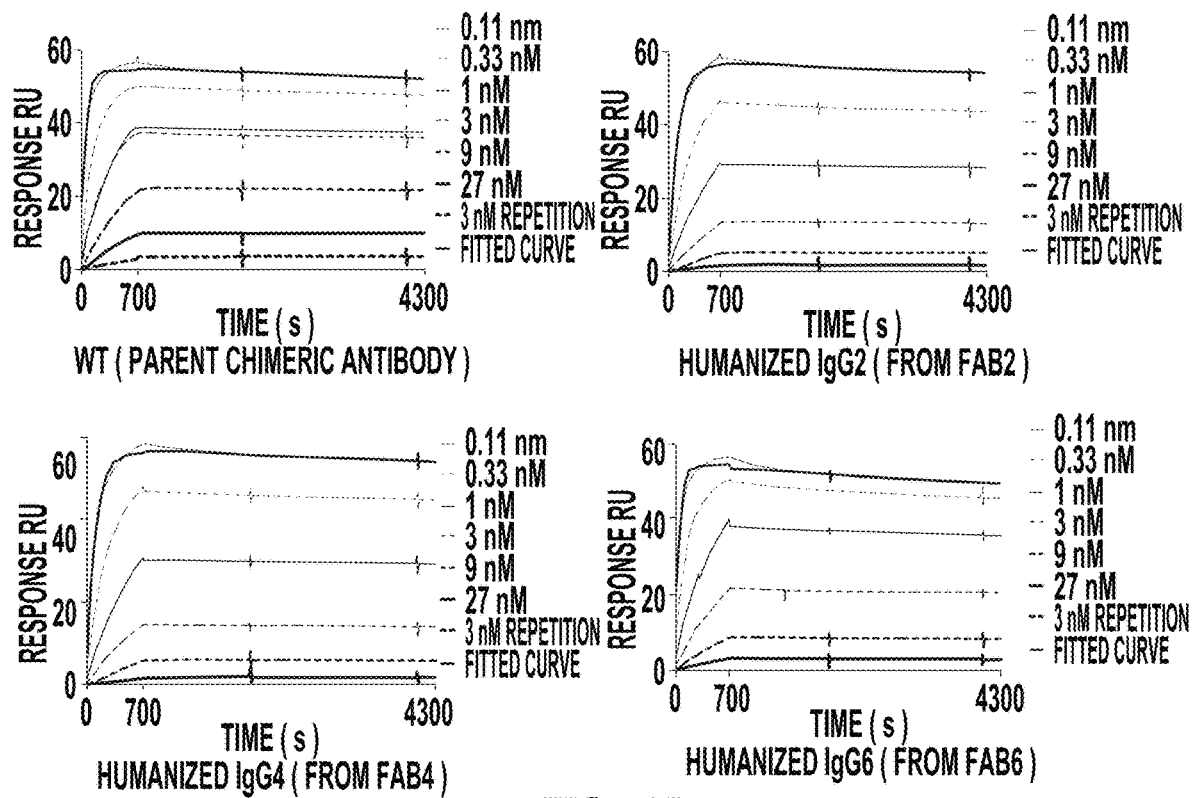
FIG. 14 provides graphs showing the fitting of BIAcore experimental data to a 1:1 binding model.

Affinity analysis of antigen-antibody interaction. Binding data of each antibody was processed and fitted to 1:1 binding model using Biacore T200 evaluation software. All experiment data could be perfectly fitted to the model (FIG. 14). As can be seen from Table 4, all humanized antibodies have comparable antigen-binding affinities to that of the parent chimeric antibody.

TABLE 4

Kinetics data of rhCD6-Fc chimera/humanized antibody interaction.

|  | $K_a$ (1/Ms) | $K_d$ (1/Ms) | $K_D$ (M) |
|---|---|---|---|
| WT (Parent chimeric antibody) | 6.7E+05 | 1.2E−05 | 1.8E−11 |
| Humanized IgG2 (from Fab2) | 3.2E+05 | 1.3E−05 | 4.2E−11 |
| Humanized IgG4 (from Fab4) | 3.5E+05 | 1.3E−05 | 3.8E−11 |
| Humanized IgG6 (from Fab6) | 6.5E+05 | 2.1E−05 | 3.2E−11 |

The FACS binding assay was also performed for validation of the Jurkat cell/humanized antibody interaction. The binding mean fluorescence intensity (MFI) & $IC_{50}$ was listed in Table 5. Three humanized antibodies show almost equal Jurkat cell binding activity as parent antibody.

TABLE 5

The binding MFI & IC$_{50}$ of humanized antibody to Jurkat cell.

| Samples/ Conc. (pM) | Humanized IgG2 | Humanized IgG4 | Humanized IgG6 | Parent chimeric IgG |
|---|---|---|---|---|
| 10000 | 42.7 | 46.7 | 45.2 | 44.4 |
| 2000 | 45 | 44.4 | 44.1 | 42.2 |
| 400 | 31 | 37 | 35.3 | 28.8 |
| 80 | 10.9 | 15 | 14.8 | 10.7 |
| 16 | 6.8 | 7.65 | 7.9 | 6.85 |
| 3.2 | 6.18 | 6.45 | 6.68 | 5.84 |
| 0 | 5.45 | 5.45 | 5.45 | 5.45 |
| IC$_{50}$ | 275.1 | 185.3 | 196.9 | 311.9 |

Figure 15:
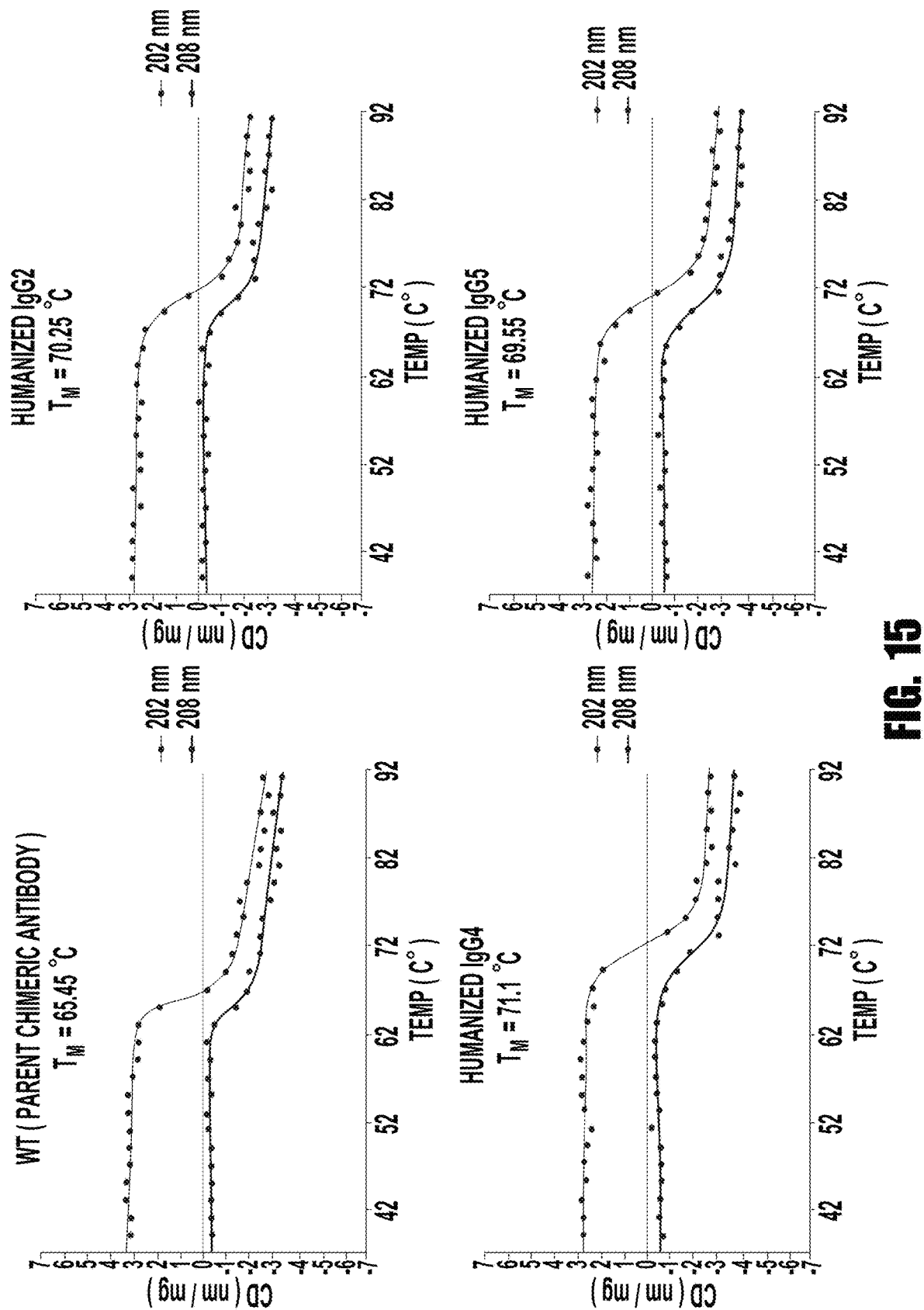
FIG. 15 provides graphs showing the temperature-induced denaturation of parent chimeric antibody and humanized antibodies monitored by the changes in ellipticity at 202 and 208 nm. Smooth curves are the fitting of CD experimental data to a two-state model.

Thermostability measurement by Circular Dichroism (CD). For all antibodies, the changes in ellipticity at 202 and 208 nm can be fitted to the two-state denaturation model perfectly (FIG. 15). The temperatures at transition midpoint (Tm) obtained by monitoring the changes in ellipticity at 202 and 208 nm and their average value are shown in Table 6. The Tm values of humanized antibodies are slightly higher than that of the parent chimeric antibody, suggesting that humanization increased its thermostability.

TABLE 6

Temperature at transition midpoint (T$_m$) of parent chimeric antibody and humanized antibodies.

| | T$_m$ (° C.) | | |
|---|---|---|---|
| | 202 nm | 208 nm | average |
| Parent chimeric antibody | 66.05 | 64.85 | 65.45 |
| Humanized IgG 2 | 70.85 | 69.65 | 70.25 |
| Humanized IgG 4 | 71.65 | 70.55 | 71.1 |
| Humanized IgG 6 | 70.15 | 68.95 | 69.55 |

CONCLUSION

In this example, anti-CD6 mouse monoclonal antibody was humanized by GenScript. Three humanized antibodies were obtained from structure-based CDR grafting and framework back-mutations. The humanized antibodies have comparable affinity to the parent antibody and better thermostability, demonstrating that the result to humanize the mouse antibodies was successful.

The complete disclosure of all patents, patent applications, and publications, and electronically available material cited herein are incorporated by reference. The foregoing detailed description and examples have been given for clarity of understanding only. No unnecessary limitations are to be understood there from. The invention is not limited to the exact details shown and described, for variations obvious to one skilled in the art will be included within the invention defined by the claims.

What is claimed is:

1. A humanized antibody or antigen-binding fragment thereof having binding specificity for CD6, wherein the antigen-binding fragment is selected from the group consisting of Fab2, Fab4, and Fab6.

2. The humanized antibody or antigen-binding fragment of claim 1, wherein the antigen-binding fragment is Fab2.

3. The humanized antibody or antigen-binding fragment of claim 1, wherein the antigen-binding fragment is Fab4.

4. The humanized antibody or antigen-binding fragment of claim 1, wherein the antigen-binding fragment is Fab6.

5. A humanized antibody or antigen-binding fragment thereof having binding specificity for CD6, wherein the humanized antibody or antigen-binding fragment comprises:
   (i) a heavy chain comprising SEQ ID NO: 1 and a light chain comprising SEQ ID NO 2;
   (ii) a heavy chain comprising SEQ ID NO: 3 and a light chain comprising SEQ ID NO: 4; or
   (iii) a heavy chain comprising SEQ ID NO: 5 and a light chain comprising SEQ ID NO: 6.

6. The humanized antibody or antigen-binding fragment of claim 5, wherein the humanized antibody or antigen-binding fragment comprises a heavy chain comprising SEQ ID NO: 1 and a light chain comprising SEQ ID NO: 2.

7. The humanized antibody or antigen-binding fragment of claim 5, wherein the humanized antibody or antigen-binding fragment comprises a heavy chain comprising SEQ ID NO: 3 and a light chain comprising SEQ ID NO: 4.

8. The humanized antibody or antigen-binding fragment of claim 5, wherein the humanized antibody or antigen-binding fragment comprises a heavy chain comprising SEQ ID NO: 5 and a light chain comprising SEQ ID NO: 6.

9. A kit comprising a humanized antibody or antigen-binding fragment thereof that specifically binds to CD6 wherein the humanized antibody or antigen-binding fragment comprises:
   (i) a heavy chain comprising SEQ ID NO: 1 and a light chain comprising SEQ ID NO 2;
   (ii) a heavy chain comprising SEQ ID NO: 3 and a light chain comprising SEQ ID NO: 4; or
   (iii) a heavy chain comprising SEQ ID NO: 5 and a light chain comprising SEQ ID NO: 6;
and a package for holding the humanized antibody or antigen-binding fragment.

10. The kit of claim 9, further comprising instructions for using the kit to carry out a method of treating a T-cell mediated disease or disorder in a subject by administering to the subject a therapeutically effective amount of the humanized antibody or antigen-binding fragment that specifically binds to CD6.

11. The kit of claim 9, wherein the disease is an autoimmune disease.

12. The kit of claim 9, wherein the T-cell mediated disease is multiple sclerosis.

13. The kit of claim 9, wherein the humanized antibody or antigen-binding fragment comprises a heavy chain comprising SEQ ID NO: 1 and a light chain comprising SEQ ID NO: 2.

14. The kit of claim 9, wherein the humanized antibody or antigen-binding fragment comprises a heavy chain comprising SEQ ID NO: 3 and a light chain comprising SEQ ID NO: 4.

15. The kit of claim 9, wherein the humanized antibody or antigen-binding fragment comprises a heavy chain comprising SEQ ID NO: 5 and a light chain comprising SEQ ID NO: 6.

16. The kit of claim 9, wherein the antigen-binding fragment is Fab2.

17. The kit of claim 9, wherein the antigen-binding fragment is Fab4.

18. The kit of claim 9, wherein the antigen-binding fragment is Fab6.

* * * * *

UNITED STATES PATENT AND TRADEMARK OFFICE
CERTIFICATE OF CORRECTION

PATENT NO. : 11,597,773 B2
APPLICATION NO. : 16/743278
DATED : March 7, 2023
INVENTOR(S) : Feng Lin and David A. Fox It is certified that error appears in the above-identified patent and that said Letters Patent is hereby corrected as shown below:

In the Specification

Column 1, Line 17, under the heading Government Funding, please amend the following paragraph:
--This invention was made with government support under EY025373 and NS081443 awarded by the National Institutes of Health. The government has certain rights in the invention.--

Signed and Sealed this
Sixteenth Day of May, 2023

Katherine Kelly Vidal
*Director of the United States Patent and Trademark Office*

SEQUENCE LISTING

<160> NUMBER OF SEQ ID NOS: 25

<210> SEQ ID NO 1
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Arg Tyr
            20                  25                  30

Ser Val His Trp Val Arg Gln Pro Pro Gly Lys Gly Leu Glu Trp Leu
        35                  40                  45

Gly Leu Ile Trp Gly Gly Gly Phe Thr Asp Tyr Asn Ser Ala Leu Lys
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Glu Gly Val Ala Tyr Trp Gly Gln Gly Thr Leu Val Thr Val Ser
            100                 105                 110

Ser

<210> SEQ ID NO 2
<211> LENGTH: 112
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 2

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asn Ser
            20                  25                  30

Asp Gly Arg Thr Tyr Leu Asn Trp Phe Gln Gln Arg Pro Gly Gln Ser
        35                  40                  45

Pro Arg Arg Leu Ile Tyr Leu Val Ser Lys Leu Asp Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Phe Thr Phe Gly Pro Gly Thr Lys Val Asp Ile Lys
            100                 105                 110

<210> SEQ ID NO 3
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Ser Arg Tyr
            20                  25                  30

Ser Val His Trp Ile Arg Gln Pro Pro Gly Lys Gly Leu Glu Trp Ile
        35                  40                  45

Gly Leu Ile Trp Gly Gly Gly Phe Thr Asp Tyr Asn Ser Ala Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Glu Gly Val Ala Tyr Trp Gly Gln Gly Thr Leu Val Thr Val Ser
            100                 105                 110

Ser

<210> SEQ ID NO 4
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asn Ser
            20                  25                  30

Asp Gly Arg Thr Tyr Leu Asn Trp Phe Gln Gln Arg Pro Gly Gln Ser
```

```
                35                  40                  45
Pro Arg Arg Leu Ile Tyr Leu Val Ser Lys Leu Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Phe Thr Phe Gly Pro Gly Thr Lys Val Asp Ile Lys
                100                 105                 110

<210> SEQ ID NO 5
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Ser Arg Tyr
                 20                  25                  30

Ser Val His Trp Ile Arg Gln Pro Pro Gly Lys Gly Leu Glu Trp Ile
             35                  40                  45

Gly Leu Ile Trp Gly Gly Gly Phe Thr Asp Tyr Asn Ser Ala Leu Lys
     50                  55                  60

Ser Arg Val Thr Ile Ser Lys Asp Asn Ser Lys Asn Gln Val Ser Leu
 65                  70                  75                  80

Lys Leu Ser Ser Val Thr Ala Ala Asp Thr Ala Val Tyr Tyr Cys Ala
                 85                  90                  95

Arg Glu Gly Val Ala Tyr Trp Gly Gln Gly Thr Leu Val Thr Val Ser
                100                 105                 110

Ser

<210> SEQ ID NO 6
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Val Val Met Thr Gln Ser Pro Leu Ser Leu Pro Val Thr Leu Gly
 1               5                  10                  15

Gln Pro Ala Ser Ile Ser Cys Lys Ser Ser Gln Ser Leu Leu Asn Ser
                 20                  25                  30

Asp Gly Arg Thr Tyr Leu Asn Trp Phe Gln Gln Arg Pro Gly Gln Ser
             35                  40                  45

Pro Arg Arg Leu Ile Tyr Leu Val Ser Lys Leu Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Phe Thr Phe Gly Pro Gly Thr Lys Val Asp Ile Lys
                100                 105                 110
```

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cttgggtgga gaggctattc                                                   20

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agccaacctt tcttctgaga gcca                                              24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgggcccaaa gcatttagct tgac                                              24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tacagagagc ttggcagtgc ttga                                              24

<210> SEQ ID NO 11
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Arg Tyr
            20                  25                  30

Ser Val His Trp Ile Arg Gln Pro Pro Gly Lys Gly Leu Glu Trp Ile
        35                  40                  45

Gly Leu Ile Trp Gly Gly Gly Phe Thr Asp Tyr Asn Ser Ala Leu Lys
    50                  55                  60

Ser Arg Val Thr Ile Ser Val Asp Thr Ser Lys Asn Gln Phe Ser Leu
65                  70                  75                  80

```
Lys Leu Ser Ser Val Thr Ala Ala Asp Thr Ala Val Tyr Tyr Cys Ala
                85                  90                  95

Arg Glu Gly Val Ala Tyr Trp Gly Gln Gly Thr Leu Val Thr Val Ser
            100                 105                 110

Ser

<210> SEQ ID NO 12
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Arg Tyr
            20                  25                  30

Ser Val His Trp Ile Arg Gln Pro Pro Gly Lys Gly Leu Glu Trp Ile
        35                  40                  45

Gly Leu Ile Trp Gly Gly Gly Phe Thr Asp Tyr Asn Ser Ala Leu Lys
    50                  55                  60

Ser Arg Val Ser Ile Thr Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Val Ala Tyr Trp Gly Gln Gly Thr Leu Val Thr Val Ser
            100                 105                 110

Ser

<210> SEQ ID NO 13
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asn Ser
            20                  25                  30

Asp Gly Arg Thr Tyr Leu Asn Trp Phe Gln Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Phe Thr Phe Gly Pro Gly Thr Lys Val Asp Ile Lys
            100                 105                 110

<210> SEQ ID NO 14
<211> LENGTH: 113
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 14

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Leu Ser Arg Tyr
            20                  25                  30

Ser Val His Trp Val Arg Gln Pro Pro Gly Lys Gly Leu Glu Trp Leu
        35                  40                  45

Gly Leu Ile Trp Gly Gly Gly Phe Thr Asp Tyr Asn Ser Ala Leu Lys
    50                  55                  60

Ser Arg Leu Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Val Ala Tyr Trp Gly Gln Gly Thr Leu Val Thr Val Ser
            100                 105                 110

Ser

<210> SEQ ID NO 15
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Gln Glu Ser Gly Pro Gly Leu Val Lys Pro Ser Glu
1               5                   10                  15

Thr Leu Ser Leu Thr Cys Thr Val Ser Gly Pro Ser Leu Ser Arg Tyr
            20                  25                  30

Ser Val His Trp Ile Arg Gln Pro Pro Gly Lys Gly Leu Glu Trp Ile
        35                  40                  45

Gly Leu Ile Trp Gly Gly Gly Phe Thr Asp Tyr Asn Ser Ala Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Glu Gly Val Ala Tyr Trp Gly Gln Gly Thr Leu Val Thr Val Ser
            100                 105                 110

Ser

<210> SEQ ID NO 16
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Arg Tyr
            20                  25                  30
```

Ser Val His Trp Val Arg Gln Pro Pro Gly Lys Gly Leu Glu Trp Leu
                35                  40                  45

Gly Leu Ile Trp Gly Gly Gly Phe Thr Asp Tyr Asn Ser Ala Leu Lys
        50                  55                  60

Ser Arg Leu Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Val Ala Tyr Trp Gly Gln Gly Thr Leu Val Thr Val Ser
                100                 105                 110

Ser

<210> SEQ ID NO 17
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Leu Ser Arg Tyr
                20                  25                  30

Ser Val His Trp Val Arg Gln Pro Pro Gly Lys Gly Leu Glu Trp Ile
                35                  40                  45

Gly Leu Ile Trp Gly Gly Gly Phe Thr Asp Tyr Asn Ser Ala Leu Lys
        50                  55                  60

Ser Arg Leu Thr Ile Ser Val Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Glu Gly Val Ala Tyr Trp Gly Gln Gly Thr Leu Val Thr Val Ser
                100                 105                 110

Ser

<210> SEQ ID NO 18
<211> LENGTH: 1398
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
gccgccacca tgggctggag ctggatcctg ctgttcctcc tgagcgtgac agcaggagtg      60
cacagccaag tccaactgca agaatcgggt ccgggcctgg tgaaaccgtc ggaaacgctg     120
tcgctgacct gtaccgtgtc gggctttagc ctgagccgtt atagcgtgca ttgggttcgc     180
cagccgccgg gtaaaggcct ggaatggctg gtgtctgattt ggggcggtgg ctttaccgat    240
tataacagcg cgctgaaaag ccgtctgacc atcagcaaag ataacagcaa aaatcaggtg     300
agcctgaaac tgagcagcgt taccgcggcc gataccgccg tgtattattg tgctcgtgaa     360
ggtgtcgcat actgggggtca aggcacgctg gttaccgtta gttccgctag caccaagggc    420
ccatcggtct tccccctggc accctcctcc aagagcacct ctgggggcac agcggccctg     480

```
ggctgcctgg tcaaggacta cttccccgaa ccggtgacgg tgtcgtggaa ctcaggcgcc    540
ctgaccagcg gcgtgcacac cttcccggct gtcctacagt cctcaggact ctactccctc    600
agcagcgtgg tgaccgtgcc ctccagcagc ttgggcaccc agacctacat ctgcaacgtg    660
aatcacaagc ccagcaacac caaggtggac aagaaagttg agcccaaatc ttgtgacaaa    720
actcacacat gcccaccgtg cccagcacct gaactcctgg ggggaccgtc agtcttcctc    780
ttccccccaa acccaagga caccctcatg atctcccgga cccctgaggt cacatgcgtg    840
gtggtggacg tgagccacga agaccctgag gtcaagttca actggtacgt ggacggcgtg    900
gaggtgcata atgccaagac aaagccgcgg gaggagcagt acaacagcac gtaccgtgtg    960
gtcagcgtcc tcaccgtcct gcaccaggac tggctgaatg gcaaggagta caagtgcaag   1020
gtctccaaca aagccctccc agcccccatc gagaaaacca tctccaaagc caagggcag   1080 ccccgagaac cacaggtgta caccctgccc ccatcccggg atgagctgac caagaaccag   1140
gtcagcctga cctgcctggt caaaggcttc tatcccagcg acatcgccgt ggagtgggag   1200
agcaatgggc agccggagaa caactacaag accacgcctc ccgtgctgga ctccgacggc   1260
tccttcttcc tctacagcaa gctcaccgtg gacaagagca ggtggcagca ggggaacgtc   1320
ttctcatgct ccgtgatgca tgaggctctg cacaaccact acacgcagaa gagcctctcc   1380
ctgtctccgg gtaaatga                                                 1398
```

<210> SEQ ID NO 19
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Ala Ala Thr Met Gly Trp Ser Trp Ile Leu Leu Phe Leu Leu Ser Val
1               5                   10                  15

Thr Ala Gly Val His Ser Gln Val Gln Leu Gln Glu Ser Gly Pro Gly
            20                  25                  30

Leu Val Lys Pro Ser Glu Thr Leu Ser Leu Thr Cys Thr Val Ser Gly
        35                  40                  45

Phe Ser Leu Ser Arg Tyr Ser Val His Trp Val Arg Gln Pro Pro Gly
    50                  55                  60

Lys Gly Leu Glu Trp Leu Gly Leu Ile Trp Gly Gly Phe Thr Asp
65                  70                  75                  80

Tyr Asn Ser Ala Leu Lys Ser Arg Leu Thr Ile Ser Lys Asp Asn Ser
                85                  90                  95

Lys Asn Gln Val Ser Leu Lys Leu Ser Ser Val Thr Ala Ala Asp Thr
            100                 105                 110

Ala Val Tyr Tyr Cys Ala Arg Glu Gly Val Ala Tyr Trp Gly Gln Gly
        115                 120                 125

Thr Leu Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190
```

```
Gln Ser Ser Gly Leu Tyr Ser Leu Ser Ser Val Val Thr Val Pro Ser
            195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465

<210> SEQ ID NO 20
<211> LENGTH: 1398
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
gccgccacca tgggctggag ctggatcctg ctgttcctcc tgagcgtgac agcaggagtg      60
cacagccaag tccaactgca agaatctggt ccgggtctgg tgaaaccgtc ggaaacgctg     120
tcgctgacgt gtaccgtgtc gggctttagc attagccgtt atagcgttca ttggattcgc     180
cagccgccgg gtaaaggcct ggaatggatt ggtctgatct gggcggtgg ctttaccgat     240 tataacagcg cgctgaaaag ccgtgtgacc atcagcaaag ataacagcaa aaatcaggtg     300
agcctgaaac tgagcagcgt taccgcggcc gataccgccg tgtattattg cgctcgtgaa     360
ggcgtcgctt actggggcca aggcaccctg gttacggtct cgtcggctag caccaagggc     420
```

-continued

```
ccatcggtct tcccctggc acctcctcc aagagcacct ctgggggcac agcggccctg    480
ggctgcctgg tcaaggacta cttccccgaa ccggtgacgg tgtcgtggaa ctcaggcgcc    540
ctgaccagcg gcgtgcacac cttcccggct gtcctacagt cctcaggact ctactccctc    600
agcagcgtgg tgaccgtgcc ctccagcagc ttgggcaccc agacctacat ctgcaacgtg    660
aatcacaagc ccagcaacac caaggtggac aagaaagttg agcccaaatc ttgtgacaaa    720
actcacacat gcccaccgtg cccagcacct gaactcctgg ggggaccgtc agtcttcctc    780
ttccccccaa aacccaagga caccctcatg atctcccgga cccctgaggt cacatgcgtg    840
gtggtggacg tgagccacga agaccctgag gtcaagttca actggtacgt ggacggcgtg    900
gaggtgcata atgccaagac aaagccgcgg gaggagcagt acaacagcac gtaccgtgtg    960
gtcagcgtcc tcaccgtcct gcaccaggac tggctgaatg gcaaggagta caagtgcaag   1020
gtctccaaca aagccctccc agcccccatc gagaaaacca tctccaaagc caaagggcag   1080
ccccgagaac cacaggtgta caccctgccc ccatcccggg atgagctgac caagaaccag   1140
gtcagcctga cctgcctggt caaaggcttc tatcccagcg acatcgccgt ggagtgggag   1200
agcaatgggc agccggagaa caactacaag accacgcctc ccgtgctgga ctccgacggc   1260
tccttcttcc tctacagcaa gctcaccgtg gacaagagca ggtggcagca ggggaacgtc   1320
ttctcatgct ccgtgatgca tgaggctctg cacaaccact acacgcagaa gagcctctcc   1380
ctgtctccgg gtaaatga                                                 1398
```

<210> SEQ ID NO 21
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Ala Ala Thr Met Gly Trp Ser Trp Ile Leu Leu Phe Leu Leu Ser Val
1               5                   10                  15

Thr Ala Gly Val His Ser Gln Val Gln Leu Gln Glu Ser Gly Pro Gly
            20                  25                  30

Leu Val Lys Pro Ser Glu Thr Leu Ser Leu Thr Cys Thr Val Ser Gly
        35                  40                  45

Phe Ser Ile Ser Arg Tyr Ser Val His Trp Ile Arg Gln Pro Pro Gly
    50                  55                  60

Lys Gly Leu Glu Trp Ile Gly Leu Ile Trp Gly Gly Gly Phe Thr Asp
65                  70                  75                  80

Tyr Asn Ser Ala Leu Lys Ser Arg Val Thr Ile Ser Lys Asp Asn Ser
                85                  90                  95

Lys Asn Gln Val Ser Leu Lys Leu Ser Ser Val Thr Ala Ala Asp Thr
            100                 105                 110

Ala Val Tyr Tyr Cys Ala Arg Glu Gly Val Ala Tyr Trp Gly Gln Gly
        115                 120                 125

Thr Leu Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
```

```
                180             185             190
Gln Ser Ser Gly Leu Tyr Ser Leu Ser Ser Val Val Thr Val Pro Ser
            195                 200                 205
Ser Ser Leu Gly Thr Gln Thr Tyr Ile Cys Asn Val Asn His Lys Pro
        210                 215                 220
Ser Asn Thr Lys Val Asp Lys Lys Val Glu Pro Lys Ser Cys Asp Lys
225                 230                 235                 240
Thr His Thr Cys Pro Pro Cys Pro Ala Pro Glu Leu Leu Gly Gly Pro
                245                 250                 255
Ser Val Phe Leu Phe Pro Pro Lys Pro Lys Asp Thr Leu Met Ile Ser
            260                 265                 270
Arg Thr Pro Glu Val Thr Cys Val Val Val Asp Val Ser His Glu Asp
        275                 280                 285
Pro Glu Val Lys Phe Asn Trp Tyr Val Asp Gly Val Glu Val His Asn
    290                 295                 300
Ala Lys Thr Lys Pro Arg Glu Glu Gln Tyr Asn Ser Thr Tyr Arg Val
305                 310                 315                 320
Val Ser Val Leu Thr Val Leu His Gln Asp Trp Leu Asn Gly Lys Glu
                325                 330                 335
Tyr Lys Cys Lys Val Ser Asn Lys Ala Leu Pro Ala Pro Ile Glu Lys
            340                 345                 350
Thr Ile Ser Lys Ala Lys Gly Gln Pro Arg Glu Pro Gln Val Tyr Thr
        355                 360                 365
Leu Pro Pro Ser Arg Asp Glu Leu Thr Lys Asn Gln Val Ser Leu Thr
    370                 375                 380
Cys Leu Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Val Leu
                405                 410                 415
Asp Ser Asp Gly Ser Phe Phe Leu Tyr Ser Lys Leu Thr Val Asp Lys
            420                 425                 430
Ser Arg Trp Gln Gln Gly Asn Val Phe Ser Cys Ser Val Met His Glu
        435                 440                 445
Ala Leu His Asn His Tyr Thr Gln Lys Ser Leu Ser Leu Ser Pro Gly
    450                 455                 460
Lys
465

<210> SEQ ID NO 22
<211> LENGTH: 1398
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gccgccacca tgggctggag ctggatcctg ctgttcctcc tgagcgtgac agcaggagtg     60
cacagccaag tccaactgca agaaagtggt ccgggcctgg tgaaaccgag tgaaaccctg    120
tctctgacgt gtaccgtgag tggctttagc ctgagccgtt atagcgttca ttggattcgc    180
cagccgccgg gtaaaggcct ggaatggatt ggtctgatct ggggcggtgg ctttaccgat    240
tataacagcg cgctgaaaag ccgtgtgacc atcagcaaag ataacagcaa aaatcaggtg    300
agcctgaaac tgagcagcgt taccgcggcc gataccgccg tgtattattg cgctcgtgaa    360
```

```
ggcgtcgctt actggggcca aggcaccctg gttaccgtct cctccgctag caccaagggc    420
ccatcggtct tccccctggc accctcctcc aagagcacct ctgggggcac agcggccctg    480
ggctgcctgg tcaaggacta cttccccgaa ccggtgacgg tgtcgtggaa ctcaggcgcc    540
ctgaccagcg gcgtgcacac cttcccggct gtcctacagt cctcaggact ctactccctc    600
agcagcgtgg tgaccgtgcc ctccagcagc ttgggcaccc agacctacat ctgcaacgtg    660
aatcacaagc ccagcaacac caaggtggac aagaaagttg agcccaaatc ttgtgacaaa    720
actcacacat gcccaccgtg cccagcacct gaactcctgg ggggaccgtc agtcttcctc    780
ttccccccaa acccaaggac acccctcatg atctcccgga cccctgaggt cacatgcgtg    840
gtggtggacg tgagccacga agaccctgag gtcaagttca actggtacgt ggacggcgtg    900
gaggtgcata atgccaagac aaagccgcgg gaggagcagt acaacagcac gtaccgtgtg    960
gtcagcgtcc tcaccgtcct gcaccaggac tggctgaatg gcaaggagta caagtgcaag   1020
gtctccaaca aagccctccc agcccccatc gagaaaacca tctccaaagc caaagggcag   1080
ccccgagaac cacaggtgta caccctgccc ccatcccggg atgagctgac caagaaccag   1140
gtcagcctga cctgcctggt caaaggcttc tatcccagcg acatcgccgt ggagtgggag   1200
agcaatgggc agccggagaa caactacaag accacgcctc ccgtgctgga ctccgacggc   1260
tccttcttcc tctacagcaa gctcaccgtg gacaagagca ggtggcagca ggggaacgtc   1320
ttctcatgct ccgtgatgca tgaggctctg cacaaccact acacgcagaa gagcctctcc   1380
ctgtctccgg gtaaatga                                                1398
```

<210> SEQ ID NO 23
<211> LENGTH: 465
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Ala Ala Thr Met Gly Trp Ser Trp Ile Leu Leu Phe Leu Leu Ser Val
1               5                   10                  15

Thr Ala Gly Val His Ser Gln Val Gln Leu Gln Glu Ser Gly Pro Gly
                20                  25                  30

Leu Val Lys Pro Ser Glu Thr Leu Ser Leu Thr Cys Thr Val Ser Gly
            35                  40                  45

Phe Ser Leu Ser Arg Tyr Ser Val His Trp Ile Arg Gln Pro Pro Gly
        50                  55                  60

Lys Gly Leu Glu Trp Ile Gly Leu Ile Trp Gly Gly Phe Thr Asp
65                  70                  75                  80

Tyr Asn Ser Ala Leu Lys Ser Arg Val Thr Ile Ser Lys Asp Asn Ser
                85                  90                  95

Lys Asn Gln Val Ser Leu Lys Leu Ser Ser Val Thr Ala Ala Asp Thr
            100                 105                 110

Ala Val Tyr Tyr Cys Ala Arg Glu Gly Val Ala Tyr Trp Gly Gln Gly
        115                 120                 125

Thr Leu Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175
```

Asn Ser Gly Ala Leu Thr Ser Gly Val His Thr Phe Pro Ala Val Leu
                180                 185                 190

Gln Ser Ser Gly Leu Tyr Ser Leu Ser Ser Val Val Thr Val Pro Ser
            195                 200                 205

Ser Ser Leu Gly Thr Gln Thr Tyr Ile Cys Asn Val Asn His Lys Pro
        210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465

<210> SEQ ID NO 24
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
gccgccacca tgggctggag ctggatcctg ctgttcctcc tgagcgtgac agcaggagtg      60
cacagcgatg tcgtgatgac gcaatccccg ctgtcgctgc cggtgacgct gggccaaccg     120
gcaagcattt cgtgtaaaag ctcgcaaagc ctgctgaaca gcgatggtcg tacctatctg     180
aattggtttc agcagcgtcc gggtcagagc ccgcgtcgtc tgatttatct ggtgagcaaa     240
ctggatagcg gtgttccgga tcgttttagc ggcagcggta gcggcaccga ttttaccctg     300

```
aaaatcagcc gcgtggaagc ggaagatgtg ggcgtttatt attgctggca gggcacccat    360
tttccgttca ccttcggtcc gggcaccaaa gttgacatta aacgaacggt ggctgcacca    420
tctgtcttca tcttcccgcc atctgatgag cagttgaaat ctggaactgc ctctgttgtg    480
tgcctgctga ataacttcta tcccagagag gccaaagtac agtggaaggt ggataacgcc    540
ctccaatcgg gtaactccca ggagagtgtc acagagcagg acagcaagga cagcacctac    600
agcctcagca gcaccctgac gctgagcaaa gcagactacg agaaacacaa agtctacgcc    660
tgcgaagtca cccatcaggg cctgagctcg cccgtcacaa agagcttcaa caggggagag    720
tgttag                                                                726
```

<210> SEQ ID NO 25
<211> LENGTH: 241
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

```
Ala Ala Thr Met Gly Trp Ser Trp Ile Leu Phe Leu Leu Ser Val
1               5                   10                  15

Thr Ala Gly Val His Ser Asp Val Val Met Thr Gln Ser Pro Leu Ser
            20                  25                  30

Leu Pro Val Thr Leu Gly Gln Pro Ala Ser Ile Ser Cys Lys Ser Ser
        35                  40                  45

Gln Ser Leu Leu Asn Ser Asp Gly Arg Thr Tyr Leu Asn Trp Phe Gln
    50                  55                  60

Gln Arg Pro Gly Gln Ser Pro Arg Arg Leu Ile Tyr Leu Val Ser Lys
65                  70                  75                  80

Leu Asp Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Trp Gln Gly Thr His Phe Pro Phe Thr Phe Gly Pro Gly
        115                 120                 125

Thr Lys Val Asp Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys
```